United States Patent
Kumar et al.

(10) Patent No.: US 10,214,521 B2
(45) Date of Patent: Feb. 26, 2019

(54) FUSED HETEROCYCLIC COMPOUNDS AS GPR120 AGONISTS

(71) Applicant: PIRAMAL ENTERPRISES LIMITED, Mumbai (IN)

(72) Inventors: Sanjay Kumar, Mumbai (IN); Rajiv Sharma, Fremont, CA (US); Sangameshwar Prabhakar Sawargave, Maharashtra (IN); Vishal Mahajan, Thane (IN)

(73) Assignee: Piramal Enterprises Limited, Mumbai (IN)

( * ) Notice: Subject to any disclaimer, the term of this patent is extended or adjusted under 35 U.S.C. 154(b) by 0 days.

(21) Appl. No.: 15/510,221

(22) PCT Filed: Sep. 9, 2015

(86) PCT No.: PCT/IB2015/056891
§ 371 (c)(1),
(2) Date: Mar. 9, 2017

(87) PCT Pub. No.: WO2016/038540
PCT Pub. Date: Mar. 17, 2016

(65) Prior Publication Data
US 2017/0283410 A1    Oct. 5, 2017

Related U.S. Application Data

(60) Provisional application No. 62/049,132, filed on Sep. 11, 2014.

(51) Int. Cl.
| | |
|---|---|
| C07D 307/80 | (2006.01) |
| A61K 31/343 | (2006.01) |
| C07D 417/10 | (2006.01) |
| C07D 491/048 | (2006.01) |
| C07D 405/10 | (2006.01) |
| C07D 409/10 | (2006.01) |
| A61P 3/10 | (2006.01) |

(52) U.S. Cl.
CPC .............. *C07D 417/10* (2013.01); *A61P 3/10* (2018.01); *C07D 405/10* (2013.01); *C07D 409/10* (2013.01); *C07D 491/048* (2013.01)

(58) Field of Classification Search
CPC .................................................. C07D 307/80
See application file for complete search history.

(56) References Cited

U.S. PATENT DOCUMENTS

| | | |
|---|---|---|
| 5,789,423 A | 8/1998 | Wakabayashi et al. |
| 8,299,296 B2 | 10/2012 | Shimada et al. |
| 8,367,708 B2 | 2/2013 | Hashimoto et al. |
| 2011/0065739 A1 | 3/2011 | Ishikawa et al. |
| 2011/0313003 A1 | 12/2011 | Shi et al. |
| 2012/0115861 A1 | 5/2012 | Calderini et al. |
| 2013/0217781 A1 | 8/2013 | Carroll et al. |
| 2014/0069963 A1 | 3/2014 | Stein |
| 2016/0347768 A1 | 12/2016 | Kumar et al. |
| 2017/0210731 A1 | 7/2017 | Kumar et al. |

FOREIGN PATENT DOCUMENTS

| | | |
|---|---|---|
| CN | 104046350 | 9/2014 |
| EP | 1 688 138 A1 | 8/2006 |
| EP | 2 125 758 | 12/2009 |
| GB | 990 397 | 4/1965 |
| GB | 1 139 607 | 1/1969 |
| WO | WO-2005/086661 | 9/2005 |
| WO | WO-2008/103500 | 8/2008 |
| WO | WO-2009/038204 | 3/2009 |
| WO | WO-2009/054479 | 4/2009 |
| WO | WO-2010/008831 | 1/2010 |
| WO | WO-2010/048207 | 4/2010 |
| WO | WO-2010/080537 | 7/2010 |
| WO | WO-2010/104195 | 9/2010 |
| WO | WO-2011/072132 | 6/2011 |
| WO | WO-2011/159297 | 12/2011 |
| WO | WO-2013/128378 A1 | 9/2013 |
| WO | WO-2013/139341 | 9/2013 |
| WO | WO-2013/185766 | 12/2013 |
| WO | WO-2014/059232 | 4/2014 |
| WO | WO-2015/125085 | 8/2015 |
| WO | WO2016022446 | * 2/2016 |

OTHER PUBLICATIONS

CAS RN 536695-50-8; STN entry date: Jun. 24, 2003. 3-(4-aminobutyl)-2-[I , I '-biphenyl]-4-yl-I H-indole-5-acetic acid.
CAS RN 536695-51-9; STN entry date: Jun. 24, 2003. 3-(4-aminobutyl)-2-[I ,I '-biphenyl]-2-yl-I H-indole-5-acetic acid.
Deng, G. et al, "Identification of benzoxazole analogs as novel, S1 P3 sparing S1P1 agonists", Bioorganic & Medicinal Chemistry Letters, 2012, vol. 22, pp. 3973-3977 Abstract; Compounds 16d, 16f, Table 3, p. 3976.
International Search Report and Written Opinion, PCT/IB2015/056891, Piramal Enterprises Ltd., Oct. 15, 2015.
Kahn and ChB. The Importance of the B-Cell in the pathogenesis of Type 2 Diabetes mellitus. The American Journal of Medicine. 2000, vol. 108 (6A0, pp. 2S-8S.
Kwon and Pessin. Adipokines mediate inflammation and insulin resistance. Front Endocrinol (Lausanne). Jun. 12, 2013;4:71.
Talukdar et al. Targeting GPR120 and other fatty acid-sensing GPCRs ameliorates insulin resistance and inflammatory diseases. Trends Pharmacol Sci. Sep. 2011;32(9):543-50.
Wild, S. et al. Global prevalence of diabetes: estimates for the year 2000 and projections for 2030. Diabetes Care. May 2004;27(5):1047-53.
CAS Registry No. 1025918-57-3, STN Entry Date Jun. 6, 2008 *** 3-(2-((2-(6-aminonaphthalen-2-yl)cyclopentyl)methoxy)phenyl)propanoic acid.

(Continued)

*Primary Examiner* — Rebecca L Anderson
*Assistant Examiner* — Karen Cheng
(74) *Attorney, Agent, or Firm* — Foley & Lardner LLP

(57) ABSTRACT

The present invention relates to fused heterocyclic compound of Formula (I), a stereoisomer, a tautomer, a pharmaceutically acceptable salt, a pharmaceutically acceptable solvate, a prodrug, a polymorph, N-oxide, S-oxide, or a carboxylic acid isostere thereof; processes for their preparation; pharmaceutical compositions comprising said compounds; and their use for the treatment of the diseases or disorders mediated by GPR120 receptor.

12 Claims, No Drawings

(56) References Cited

OTHER PUBLICATIONS

CAS Registry No. 1026475-19-3, STN Entry Date Jun. 8, 2008 *** 2-[[2-[6-(carboxymethoxy)-2-naphthalenyl]cyclohexyl]methoxy]-benzenepropanoic acid.
CAS Registry No. 1026489-82-6, STN Entry Date Jun. 8, 2008 *** methyl 3-(2-((2-(6-aminonaphthalen-2-yl)cyclopentyl)methoxy)phenyl)propanoate.
CAS Registry No. 1026500-58-2, STN Entry Date Jun. 8, 2008 *** 6-[2-[[2-(2-carboxyethyl)phenoxy]methyl]cyclohexyl]-2-naphthalenecarboxylic acid.
CAS Registry No. 1027427-54-8, STN Entry Date Jun. 11, 2008 *** 2-[[2-(7-amino-2-naphthalenyl)cyclopentyl]methoxy]-benzenepropanoic acid.
CAS Registry No. 1027654-19-8, STN Entry Date Jun. 12, 2008 *** 6-[2-[[2-(3-methoxy-3-oxopropyl)phenoxy]methyl]cyclohexyl]-2-naphthalenecarboxylic acid.
CAS Registry No. 1027894-93-4, STN Entry Date Jun. 13, 2008 *** 2-[[2-(7-amino-2-naphthalenyl)cyclopentyl]methoxy]-benzenepropanoic acid methyl ester.
CAS Registry No. 1287459-87-3, STN Entry Date Apr. 29, 2011 *** rel-3-[[[(2R,3S)-2-(2-fluoro-5-methoxyphenyl)-6-oxo-3-piperidinyl]amino]methyl]-1H-indole-1-acetamide.
CAS Registry No. 1287467-25-7, STN Entry Date Apr. 29, 2011 *** rel-3-[[[(2R,3S)-2-(2-fluoro-5-methmophenyl)-6-oxo-3-piperidinyl]amino]methyl]-1H-indole-1-propanamide.
CAS Registry No. 1346947-23-6, STN Entry Date Dec. 1, 2011 *** 3,4-dihydro-7-[[[(3R,4R)-4-[4-[3-[(2-methoxyphenyl)methoxy]propoxy]phenyl]-3-piperidinyl]oxy]methyl]-1(2H)-quinolineethanesulfonamide.
CAS Registry No. 1347559-94-7, STN Entry Date Dec. 2, 2011 *** 3-[[[(2S,3S)-2-phenyl-3-piperidinyl]amino]methyl]-4-(2,2,2-trifluoroethoxy)-benzeneacetamide.
CAS Registry No. 1553145-75-7, Stn Entry Date Feb. 23, 2014 *** 5-[[[2-(1H-imidazol-1-yl)cyclopentyl]amino]methyl]-2-thiopheneacetic acid.
CAS Registry No. 1627272-79-0, STN Entry Date Sep. 28, 2014 *** methyl 2-(4-(((2-phenyltetrahydro-2H-pyran-3-yl)methyl)amino)-1H-pyrazolo[3,4-d]pyrimidin-1-yl)acetate.
CAS Registry No. 1645359-44-9, STN Entry Date Feb. 8, 2015 *** N-methyl-4-[[(2-phenylcyclopentyl)amino]methyl]-2-thiazoleacetamide.
CAS Registry No. 173160-56-0, STN Entry Date Feb. 13, 1996 *** [1S-(exo,exo)]-2-[[3-[4-[[(4-cyclohexylbutyl)amino]carbonyl]-2-oxazolyl]-7-oxabicyclo[2.2.1]hept-2-yl]methoxy]-benzeneacetic acid.
Duncton et al., "Preparation of Heteroaryloxetanes and Heteroarylazetidines by Use of a Minisci Reaction", J. Org. Chem., (2009), 74(16):6354-6357.
Guda et al., "An efficient synthesis of styryl 1,3,4-thiadiazoles using Lawesson's reagent and propylphosphonic anhydride-precursors for bis heterocycles", Arabian Journal of Chemistry (2014) 7, 947-954 (available online Aug. 29, 2014).
Marhraoui et al., "Synthese de nouveaux glycosyl-1,2,3-triazoles 1,4-disubstitues", J. Maroc. Chim. Hétérocyclique., 2010, 9(1):59-67. (No Abstract Available).
Muralkirishna et al., "Synthesis, antimicrobial and cytotoxic activities of sulfone linked bis heterocycles", European Journal of Medicinal Chemistry, 2012, 54:605-614.
National Diabetes Statistics Report (2014)(12 pages).
Padmaja et al., "Synthesis and antimicrobial activity of pyrrolyl/pyrazolyl arylaminosulfonylmethyl 1,3,4-oxadiazoles, 1,3,4-thiadiazoles and 1,2,4-triazoles", Chem. Pharm. Bull., 2011, 59(11)1509-1517.
Paulsen et al., "Expression of the Fatty Acid Receptor GPR120 in the Gut of Diet-Induced-Obese Rats and Its Role in GLP-1 Secretion", PLOS one, 2014, 9(2):e88227, pp. 1-6.
PCT International Search Report and Written Opinion for Application No. PCT/IB2015/051232 dated May 18, 2015.
PCT International Search Report and Written Opinion for Application No. PCT/IB2015/055572 dated Jan. 21, 2016. (17 pages).
Reddy et al., "Synthesis and antioxidant activity of a new class of mono- and bis-heterocycles", Arch. Pharm. Chem. Life Sci., 2013, 346:154-162.
Reddy et al., "Synthesis and antioxidant activity of styrylsulfonylmethyl 1,3,4-oxadiazoles, pyrazolyl/isoxazolyl-1,3,4-oxadiazoles", Chem. Pharm. Bull., 2013, 61(12):1291-1297.
Shimpukade et al., "Discovery of a Potent and Selective GPR120 Agonist", J. Med. Chem., 2012, 55:4511-4515.
Siddiqui et al., "BRET biosensor analysis of receptor tyrosine kinase functionality", Frontiers in Endocrinology, (2013), vol. 4, article 46, p. 1-11.
Suckow et al., "Alteration of the Glucagon Axis in GPR120 (FFAR4) Knockout Mice. A Role for GPR120 in Glucagon Secretion", J. Biol Chem., 2014, 289(22):15751-15763.
Concise Encyclopedia Chemistry (1993) Walter de Gruyter Berlin New York, pp. 872-873.
EP Supplementary Search Report for Application No. 15824099.4 dated Dec. 12, 2017. (9 pages).
Guda et al., "An efficient synthesis of styryl 1,3,4-thiadiazoles using Lawesson's reagent and Propylphosphonic anhydride-precursors for bis heterocycles", Arabian Journal of Chemistry, 2014, 7:947-954.
PCT International Preliminary Report on Patentability (Chapter 1) for Application No. PCT/182015/055572 dated Jan. 31, 2017. (11 pages).
Vippagunta et al., "Crystalline solids", Advanced Drug Delivery Reviews, 2001;48:3-26.

* cited by examiner

FUSED HETEROCYCLIC COMPOUNDS AS GPR120 AGONISTS

CROSS-REFERENCE TO RELATED APPLICATIONS

This application is a U.S. National Stage Application of PCT/IB2015/056891, filed Sep. 9, 2015, which claims the benefit of and priority to U.S. Provisional Patent Application No. 62/049,132, filed Sep. 11, 2014.

FIELD OF THE INVENTION

The present invention relates to fused heterocyclic compounds represented by the compounds of Formula (I) (as described herein); processes for their preparation; pharmaceutical compositions comprising said compounds; and methods of using said compounds for the treatment or prophylaxis of the diseases or disorders mediated by GPR120 receptor.

BACKGROUND OF THE INVENTION

Metabolic diseases or disorders are caused by an abnormal metabolic process and may either be congenital due to an inherited enzyme abnormality or acquired due to a disease of an endocrine organ or failure of a metabolically important organ such as the liver or the pancreas.

Among the metabolic disorders, diabetes mellitus is the most prevalent and is considered to be one of the five leading causes of death in the world (Diabetes Care, vol. 27, 2004, pp. 1047-1053). Diabetes mellitus is typically classified into two main subtypes: Type 1 and Type 2 diabetes mellitus. Type 1 diabetes mellitus (otherwise known as Insulin Dependent Diabetes Mellitus, IDDM), which generally occurs in adolescents under 20 years of age, is an autoimmune disease causing an insulitis with the subsequent destruction of insulin-producing β-cells of the pancreas. Further, in latent autoimmune diabetes in adults (LADA), β-cells are destroyed due to autoimmune attack. The subsequent lack of insulin leads to elevated levels of blood and urine glucose (hyperglycemia). Although the exact trigger for this autoimmune response is not known, patients with Type 1 diabetes have high levels of antibodies against pancreatic beta cells (hereinafter "beta cells"). However, it cannot be ascertained that all patients with high levels of these antibodies develop Type 1 diabetes. Type 2 diabetes mellitus or non-insulin-dependent diabetes mellitus (NIDDM) is developed when human muscle, fat and liver cells are not able to respond normally to insulin that body secretes. This inability to respond, otherwise known as insulin resistance, may be due to restriction on the numbers of insulin receptors on these cells, or a dysfunctional behaviour of signalling pathways within the cells, or both. Initially, the β-cells which are responsible for the production of insulin, compensate for this insulin resistance by increasing their insulin secretion. However, these cells gradually become unable to produce enough insulin to facilitate the normal glucose homeostasis, causing the progression to Type 2 diabetes (Am J Med. 108(6), Supplement 1, 2000, pp. 2S-8S). Type 2 diabetes (T2D) is characterised by fasting hyperglycemia which occurs as an effect of the combined lesions of insulin resistance and β-cell dysfunction. There are two types of defects associated with the β-cells: the first component, an increase in the basal insulin release which usually occurs in the presence of low, non-stimulatory glucose concentrations. The second component is a failure to enhance the insulin release in response to a hyperglycaemia challenge.

Obesity is another risk factor for developing metabolic diseases or disorders such as diabetes, cardiovascular disorders, hypertension, hyperlipidemia and an increased mortality. Diabetes caused by insulin resistance and obesity are part of the "metabolic syndrome" which is defined as the linkage between several diseases (also referred to as syndrome X, insulin-resistance syndrome, or deadly quartet). These often occur in the same patients and are major risk factors for the development of Type 2 diabetes and cardiovascular diseases (Frontiers in Endocrinology, vol. 4, 2013, pp. 1-11). It has been suggested that the control of lipid levels and/or glucose levels is required to treat type 2 diabetes and cardiovascular diseases. Even though lifestyle changes like exercise and healthy diet are regarded as the most efficient ways to prevent and manage the disease, pharmaceutical intervention is frequently necessary.

Current treatment options for diabetes, particularly T2D, include use of hypoglycemic agents and insulin. Metformin is one such hypoglycemic agent which is used in the treatment of Type 2 diabetes. It is, in fact, one of the oldest drugs used for the treatment of T2D and it still remains the drug of choice despite associated gastrointestinal (GI) side effects including anorexia, nausea, diarrhea and vomiting commonly associated with it. In fact, metformin should be used with caution in patients with renal impairment because of the slight risk of lactic acidosis. Sulfonylureas (SUs) e.g. glimepiride, glipizide, are insulin secretagogues, which act on β-cells to increase insulin release, are commonly used in the treatment of Type 2 diabetes. However, use of sulfonylureas is also associated with adverse effects in that they increase the risk of hypoglycemia and lead to weight gain. Insulin treatment which is chosen by patients carries the same side-effects. Thiazolidinedione compounds e.g. rosiglitazone, pioglitazone, are insulin sensitizers which bind to peroxisome proliferator-activated receptors (PPARs) in cells and thereby increase the insulin sensitivity. Though, thiazolidinedione compounds have also been widely used, the enhanced risks of cardiovascular disease and hepatotoxicity have resulted in stringent limitations on their use. Relatively recently, regulatory authorities approved new classes of anti-diabetic agents such as GLP-1 agonists (exenatide and liraglutide) and DPP-4 inhibitors (linagliptin and alogliptin).

It is a known fact that metabolic processes are regulated by fatty acids which are important biological molecules that serve both as a source of energy and as signalling molecules. Generally, it is believed that fatty acids produce their biological effects through interacting with intracellular targets including, for example, the family of peroxisome proliferator-activated receptors (PPARs). However, in the recent years it has become clear that fatty acids also serve as agonists for a group of cell surface G protein-coupled receptors (GPCRs). Free fatty acids (FFAs) have been demonstrated to act as ligands of several GPCRs including GPR40 (FFAR1), GPR43, GPR84, GPR119 and GPR120. One of the GPCR namely GPR40 facilitates glucose-stimulated insulin secretion from pancreatic β-cells, whereas the other GPCR namely GPR120 regulates the secretion of glucagon-like peptide-1 (GLP-1) in the intestine, as well as insulin sensitivity in macrophages. GPR120 is localized to intestinal enteroendocrine cells, such as colonic L cells. Certain research studies conducted relatively recently identified that loss-of-function of GPR120 human variant is associated with obesity, diabetes and other insulin resistance, and related metabolic disorders and also with inflammatory disorders. These findings establish GPR120 as a potential target for the treatment of diabetes, other metabolic disorders and also, inflammatory disorders (Trends Pharmacol Sci. vol. 32(9), 2011 pp. 543-550).

Various patent documents describe compounds which are reported to be GPR120 modulators. Examples of patent documents describing GPR120 modulators include WO2008103500, WO2009038204, WO2010008831, WO2010048207, WO2010080537, WO2010104195, WO2011072132, WO2013139341, WO2013185766, EP2125758A1, US2011065739 and U.S. Pat. No. 8,367,708.

Thus, in view of the role of GPR120 receptor in potentiating metabolic disorders such as diabetes and also, inflammatory disorders, there is need in the art to develop compounds that act by modulating the GPR120 receptor pathways.

SUMMARY OF THE INVENTION

In one aspect, the present invention relates to a compound of Formula (I) (as described herein) or an isotopic form, a stereoisomer, a tautomer, a pharmaceutically acceptable salt, a pharmaceutically acceptable solvate, a prodrug, a polymorph, N-oxide, S-oxide, or a carboxylic acid isostere thereof.

In another aspect of the present invention, there is provided a process for the preparation of the compound of Formula (I) or a pharmaceutically acceptable salt thereof.

In a further aspect, the present invention relates to a pharmaceutical composition comprising a therapeutically effective amount of a compound of Formula (I) or a stereoisomer, a tautomer a pharmaceutically acceptable salt or a pharmaceutically acceptable solvate thereof; and at least one pharmaceutically acceptable carrier or excipient.

In a further aspect, the present invention relates to a pharmaceutical composition comprising a therapeutically effective amount of a compound of Formula (I) or a stereoisomer, a tautomer, a pharmaceutically acceptable salt or a pharmaceutically acceptable solvate thereof; and one further therapeutically active agent and at least one pharmaceutically acceptable carrier or excipient.

In an aspect, the present invention relates to the compound of Formula (I) or a stereoisomer, a tautomer, a pharmaceutically acceptable salt or a pharmaceutically acceptable solvate thereof; for use as GPR120 agonist.

In another further aspect, the present invention relates to a method for modulating GPR120 function in a cell, comprising contacting a cell with an effective amount of a compound of Formula (I) or a stereoisomer, a tautomer, a pharmaceutically acceptable salt or a pharmaceutically acceptable solvate thereof.

In yet another aspect, the present invention provides a compound of Formula (I) or a stereoisomer, a tautomer, a pharmaceutically acceptable salt or a pharmaceutically acceptable solvate thereof; for use in the treatment or prophylaxis of a disease or a disorder mediated by GPR120.

In yet another further aspect, the present invention provides a method for the treatment or prophylaxis of a disease or a disorder mediated by GPR120, comprising administering to a subject in need thereof; a therapeutically effective amount of the compound of Formula (I) or a stereoisomer, a tautomer, a pharmaceutically acceptable salt or a pharmaceutically acceptable solvate thereof.

In a still further aspect, the present invention relates to use of the compound of Formula (I) or a stereoisomer, a tautomer, a pharmaceutically acceptable salt or a pharmaceutically acceptable solvate thereof; in the manufacture of a medicament, for the treatment or prophylaxis of a disease or a disorder mediated by GPR120.

In another further aspect, the present invention relates to use of the compound of Formula (I) or a stereoisomer, a tautomer, a pharmaceutically acceptable salt or a pharmaceutically acceptable solvate thereof; in combination with one further therapeutically active agent for the treatment or prophylaxis of a disease or a disorder mediated by GPR120.

These and other objectives and advantages of the present invention will be apparent to those skilled in the art from the following description.

DETAILED DESCRIPTION OF THE INVENTION

In one aspect, the present invention relates to a compound of Formula (I),

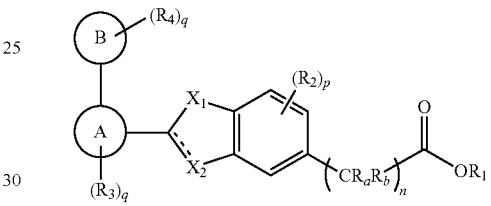

Formula (I)

wherein, $X_1$ is —O—, —S— or —NR';

$X_2$ is —O—, —S—, —N—, —NR'—, —CR'— or —CR'R"—;

Ring A is $(C_6-C_{10})$aryl or 5- to 10-membered heteroaryl;

Ring B is $(C_3-C_8)$cycloalkyl, $(C_5-C_8)$cycloalkenyl, $(C_6-C_{10})$aryl, 5- to 10-membered heteroaryl or a saturated or partially unsaturated 3- to 11-membered heterocyclyl ring containing one to four heteroatoms independently selected from the group consisting of O, N and S;

$R_1$ is hydrogen or $(C_1-C_6)$alkyl;

$R_2$ at each occurrence is independently selected from the group consisting of hydrogen, halogen, hydroxy, cyano, nitro, —$NR_5R_6$, —$C(O)R_5$, —$C(O)NR_5R_6$, —$S(O)_rR_7$, $(C_1-C_6)$alkyl, halo$(C_1-C_6)$alkyl, —$O(C_1-C_6)$alkyl and $(C_6-C_{10})$aryl;

$R_3$ and $R_4$ at each occurrence are independently selected from the group consisting of hydrogen, halogen, oxo, cyano, nitro, —$NR_5R_6$, —$C(O)R_5$, —$C(O)NR_5R_6$, —$S(O)_rR_7$, $(C_1-C_6)$alkyl, halo$(C_1-C_6)$alkyl, hydroxy, —$O(C_1-C_6)$alkyl, —$(C_3-C_8)$cycloalkyl, $(C_6-C_{10})$aryl, —$O(C_1-C_6)$aryl, heterocyclyl and heteroaryl;

$R_5$ and $R_6$ at each occurrence are independently selected from the group consisting of hydrogen, $(C_1-C_6)$alkyl, $(C_6-C_{10})$aryl, heterocyclyl and heteroaryl;

$R_7$ is hydrogen, $(C_1-C_6)$alkyl or —$NR_5R_6$;

R' and R" at each occurrence are independently selected from the group consisting of hydrogen, $(C_1-C_6)$alkyl, —$C(O)(C_1-C_6)$alkyl, —$C(O)O(C_1-C_6)$alkyl and —$S(O)_2(C_1-C_6)$alkyl; or R' and R" are taken together to form oxo, $(C_3-C_8)$cycloalkyl, $(C_5-C_8)$cycloalkenyl, or 3- to 6-membered saturated or a partially unsaturated heterocyclyl ring containing one or two heteroatoms independently selected from the group consisting of O, N and S;

$R_a$ and $R_b$ at each occurrence are independently selected from the group consisting of hydrogen, halogen and $(C_1-C_6)$alkyl;

n is an integer from 1 to 6;

p is an integer from 1 to 3;

q is an integer from 1 to 4;

t is an integer from 0 to 2;

------- represents presence or absence of a single bond;

wherein, $(C_1-C_6)$alkyl is unsubstituted or substituted with one or more groups independently selected from the group consisting of halogen, hydroxy, cyano, nitro, —$NR_5R_6$, —$C(O)R_5$, —$C(O)NR_5R_6$, —$S(O)_tR_7$, $(C_1-C_6)$alkyl, halo$(C_1-C_6)$alkyl, —$O(C_1-C_6)$alkyl, $(C_6-C_{10})$aryl, $(C_3-C_8)$cycloalkyl, heterocyclyl and heteroaryl; wherein $R_5$, $R_6$, $R_7$ and t are as defined above;

—$O(C_1-C_6)$alkyl is unsubstituted or substituted with one or more groups independently selected from the group consisting of halogen, hydroxy, cyano, nitro, —$NR_5R_6$, —$C(O)R_5$, —$C(O)NR_5R_6$, —$S(O)_tR_7$, $(C_1-C_6)$alkyl, halo$(C_1-C_6)$alkyl, $(C_6-C_{10})$aryl, $(C_3-C_8)$cycloalkyl, heterocyclyl and heteroaryl; wherein $R_5$, $R_6$, $R_7$ and t are as defined above;

$(C_3-C_8)$cycloalkyl is unsubstituted or substituted with one or more groups independently selected from the group consisting of oxo, halogen, hydroxy, cyano, nitro, —$NR_5R_6$, —$C(O)R_5$, —$C(O)NR_5R_6$, —$S(O)_tR_7$, $(C_1-C_6)$alkyl, halo$(C_1-C_6)$alkyl and —$O(C_1-C_6)$alkyl; wherein $R_5$, $R_6$, $R_7$ and t are as defined above;

$(C_5-C_8)$cycloalkenyl is unsubstituted or substituted with one or more groups independently selected from the group consisting of halogen, hydroxy, cyano, nitro, —$NR_5R_6$, —$C(O)R_5$, —$C(O)NR_5R_6$, —$S(O)_tR_7$, $(C_1-C_6)$alkyl, halo$(C_1-C_6)$alkyl and —$O(C_1-C_6)$alkyl; wherein $R_5$, $R_6$, $R_7$ and t are as defined above;

$(C_6-C_{10})$aryl is unsubstituted or substituted with one or more groups independently selected from the group consisting of halogen, hydroxy, cyano, nitro, —$C(O)R_5$, —$C(O)OR_5$, —$S(O)_tR_7$, —$NR_5R_6$, $(C_1-C_6)$alkyl, halo$(C_1-C_6)$alkyl, —$O(C_1-C_6)$alkyl, halo$(C_1-C_6)$alkoxy, $(C_3-C_8)$cycloalkyl, $(C_6-C_{10})$aryl, —$O(C_6-C_{10})$aryl, heterocyclyl and heteroaryl, wherein $R_5$, $R_6$, $R_7$ and t are as defined above;

heterocyclyl is a 3- to 11-membered ring, which is unsubstituted or substituted with one or more groups independently selected from the group consisting of halogen, hydroxy, cyano, nitro, —$C(O)R_5$, —$C(O)OR_5$, —$S(O)_tR_7$, —$NR_5R_6$, $(C_1-C_6)$alkyl, halo$(C_1-C_6)$alkyl, —$O(C_1-C_6)$alkyl, halo$(C_1-C_6)$alkoxy, $(C_3-C_8)$cycloalkyl, $(C_6-C_{10})$aryl, heterocyclyl and heteroaryl; wherein $R_5$, $R_6$, $R_7$ and t are as defined above;

heteroaryl is a 5- to 10-membered ring, which is unsubstituted or substituted with one or more groups independently selected from the group consisting of halogen, hydroxy, cyano, nitro, —$C(O)R_5$, —$C(O)OR_5$, —$S(O)_tR_7$, —$NR_5R_6$, $(C_1-C_6)$alkyl, halo$(C_1-C_6)$alkyl, —$O(C_1-C_6)$alkyl, halo$(C_1-C_6)$alkoxy, $(C_3-C_8)$cycloalkyl, $(C_6-C_{10})$aryl, heterocyclyl and heteroaryl; wherein $R_5$, $R_6$, $R_7$ and t are as defined above;

halogen is chlorine, bromine, iodine or fluorine;

or an isotopic form, a stereoisomer, a tautomer, a pharmaceutically acceptable salt, a pharmaceutically acceptable solvate, a prodrug, a polymorph, N-oxide, S-oxide, or a carboxylic acid isostere thereof.

Definitions

Unless otherwise indicated, the following definitions are set forth to illustrate and define the meaning and scope of the various terms used to describe the invention herein and the appended claims. These definitions should not be interpreted in the literal sense as they are not intended to be general definitions and are relevant only for this application.

The singular forms "a", "an" and "the" include plural aspects unless the context clearly dictates otherwise. For instance, the terms "a", "an" and "the" refers to "one or more" when used in the subject specification, including the claims. Thus, for example, reference to "a compound" may include a plurality of such compounds, or reference to "a disease" or "a disorder" includes a plurality of diseases or disorders.

Also, use of "(s)" as part of a term, includes reference to the term singly or in plurality, for example, the term pharmaceutically acceptable salt(s) indicates a single salt or more than one salt of the compound of formula (I).

The term "or" is generally employed in its sense including "and/or" unless the content clearly dictates otherwise.

As used herein, the term "halogen" refers to chlorine, fluorine, bromine or iodine atom.

As used herein, the term "$(C_1-C_6)$alkyl" or "alkyl" alone or as part of another group, refers to the radical of saturated aliphatic groups, including straight or branched-chain alkyl groups. A straight-chain or branched chain alkyl has six or fewer carbon atoms in its backbone, for instance, $C_1-C_6$ for straight chain and $C_3-C_6$ for branched chain. As used herein, $(C_1-C_6)$alkyl refers to an alkyl group having from 1 to 6 carbon atoms. Representative examples of alkyl include, but are not limited to, methyl, ethyl, n-propyl, n-butyl, n-pentyl, n-hexyl, isopropyl, sec-butyl, isobutyl, tert-butyl, isopentyl, 2-methylbutyl and 3-methylbutyl.

Furthermore, unless stated otherwise, the alkyl group can be unsubstituted or substituted with one or more substituents, for example, from one to four substituents, independently selected from the group consisting of halogen, hydroxy, cyano, nitro, —$NR_5R_6$, —$C(O)R_5$, —$C(O)OR_5$, —$C(O)NR_5R_6$, —$S(O)_tR_7$, $(C_1-C_6)$alkyl, halo$(C_1-C_6)$alkyl, —$O(C_1-C_6)$alkyl, halo$(C_1-C_6)$alkoxy, $(C_3-C_{10})$cycloalkyl, $(C_6-C_{10})$aryl, heterocyclyl, heteroaryl and —$C(O)NHS(O)_tR_7$, wherein $R_5$, $R_6$, $R_7$ and t are as defined above. Examples of substituted alkyl include, but are not limited to hydroxymethyl, 2-chlorobutyl, trifluoromethyl, aminoethyl and benzyl.

As used herein, the term "halo$(C_1-C_6)$alkyl" or "haloalkyl" refers to alkyl groups as defined above wherein one or more hydrogen atom of same or different carbon atoms of the alkyl group are substituted with same or different halogens. A monohalo$(C_1-C_6)$alkyl radical, for example, can have a chlorine, bromine, iodine or fluorine atom. Dihalo or polyhalo$(C_1-C_6)$alkyl radicals can have two or more of the same or different halogen atoms. Representative examples of halo$(C_1-C_6)$alkyl include, but are not limited to, chloromethyl, dichloromethyl, trichloromethyl, dichloroethyl, dichloropropyl, fluoromethyl, difluoromethyl, trifluoromethyl, pentafluoroethyl, heptafluoropropyl, difluorochloromethyl, dichlorofluoromethyl, difluoroethyl and difluoropropyl.

As used herein, the term "$(C_1-C_6)$alkoxy" or "alkoxy" refers to a $(C_1-C_6)$alkyl having an oxygen radical attached thereto. The terms "$(C_1-C_6)$alkoxy" or "—$O(C_1-C_6)$-alkyl" or alkoxy wherever used in this specification have the same meaning. Representative examples of alkoxy groups include, but are not limited to, methoxy, ethoxy, propoxy, isopropoxy, n-butoxy, isobutoxy and tert-butoxy. Furthermore, unless stated otherwise, the alkoxy groups can be unsubstituted or substituted with one or more groups. A substituted alkoxy refers to a $(C_1-C_6)$alkoxy substituted with one or more groups, particularly one to four groups independently selected from the groups indicated above as the substituents for the alkyl group.

As used herein, the term "haloalkoxy" or "halo($C_1$-$C_6$) alkoxy" refers to radicals wherein one or more of the hydrogen atoms of same or different carbon atoms of the alkoxy group are substituted with same or different halogens. Representative examples of "haloalkoxy" or "halo($C_1$-$C_6$)alkoxy" groups include, but are not limited to, difluoromethoxy ($OCHF_2$), trifluoromethoxy ($OCF_3$) and trifluoroethoxy ($OCH_2CF_3$).

As used herein, the term "($C_3$-$C_8$)cycloalkyl" or "cycloalkyl" refers to a saturated monocyclic hydrocarbon ring containing three to eight carbon atoms. Representative ($C_3$-$C_8$)cycloalkyl groups include, but are not limited to, cyclopropyl, cyclobutyl, cyclopentyl, cyclohexyl, cycloheptyl and cyclooctyl. Unless stated otherwise, ($C_3$-$C_8$)cycloalkyl can be unsubstituted or substituted with one or more substituents, for example 1-5 substituents independently selected from the group consisting of oxo, halogen, hydroxy, cyano, nitro, $-NR_5R_6$, $-C(O)R_5$, $-C(O)NR_5R_6$, $-S(O)_tR_7$, ($C_1$-$C_6$)alkyl, halo($C_1$-$C_6$)alkyl, $-O(C_1$-$C_6)$ alkyl, ($C_3$-$C_8$)cycloalkyl, ($C_6$-$C_{10}$)aryl, heterocyclyl and heteroaryl; wherein $R_5$, $R_6$, $R_7$ and t are as defined above. Cycloalkyl group comprises a saturated cycloalkyl ring system which does not contain any double bond within the ring or a partially unsaturated cycloalkyl ring system which may contain one or more double bonds within the ring system that is stable, and do not form an aromatic ring system.

As used herein, the term "($C_5$-$C_8$)cycloalkenyl" or "cycloalkenyl" refers to a partially unsaturated monocyclic hydrocarbon ring containing five to eight carbon atoms that is stable. The ring system contains at least one double bond and does not form an aromatic ring system. A substituted "cycloalkenyl refers to a ($C_5$-$C_8$)cycloalkenyl substituted with one or more groups, for example 1-5 groups selected from the groups indicated above as the substituents for the cycloalkyl group.

The term "($C_6$-$C_{10}$)aryl" or "aryl" as used herein refers to monocyclic or bicyclic hydrocarbon groups having 6 to 10 ring carbon atoms, wherein at least one carbocyclic ring is having a t electron system. Examples of ($C_6$-$C_{10}$) aryl ring systems include, but are not limited to, phenyl and naphthyl. Unless indicated otherwise, aryl group can be unsubstituted or substituted with one or more substituents, for example 1-4 substituents independently selected from the group consisting of halogen, hydroxy, cyano, nitro, $-C(O)R_5$, $-C(O)$ $OR_5$, $-S(O)_tR_7$, $-NR_5R_6$, ($C_1$-$C_6$)alkyl, halo($C_1$-$C_6$)alkyl, $-O(C_1$-$C_6)$alkyl, halo($C_1$-$C_6$)alkoxy, ($C_3$-$C_8$)cycloalkyl, ($C_6$-$C_{10}$)aryl, $-O(C_6$-$C_{10})$aryl, heterocyclyl and heteroaryl; wherein $R_5$, $R_6$, $R_7$ and t are as defined above.

The aryl group can be substituted in any desired position. For example, in monosubstituted phenyl, the substitutent may be located in the 2-position, the 3-position, the 4-position or the 5-position. If the phenyl carries two substituents, they can be located in 2,3-position, 2,4-position, 2,5-position, 2,6-position, 3,4-position or 3,5-position. Representative examples of monosubstituted phenyl groups include, but are not limited to, 3-trifluoromethylphenyl, 4-chlorophenyl and 4-cyanophenyl. Examples of disubstituted phenyl groups include, but are not limited to, 4-methoxy-3-trifluoromethylphenyl, 2-methoxy-5-trifluoromethylphenyl, xylene, 1,2-dimethoxyphenyl and 2-fluoro-3-trifluoromethylphenyl.

As used herein, the term "$-O(C_6$-$C_{10})$aryl" refers to ($C_6$-$C_{10}$)aryl group having an oxygen radical attached thereto. The terms aryloxy or $-O(C_6$-$C_{10})$aryl wherever used in this specification have the same meaning. Representative example includes, but is not limited to, phenoxy. Furthermore, unless stated otherwise, the $-O(C_6$-$C_{10})$aryl group can be unsubstituted or substituted with one or more groups. A substituted $-O(C_6$-$C_{10})$aryl refers to a ($C_6$-$C_{10}$) aryl group having an oxygen radical attached thereto and substituted with one or more groups, for example 1-5 groups selected from the groups indicated above as the substituents for the ($C_6$-$C_{10}$)aryl group.

As used herein, the terms "heterocycle", "heterocyclyl" or "heterocyclic", refer to a 3- to 11-membered, saturated or partially unsaturated monocyclic or bicyclic ring system containing 1 to 4 heteroatoms independently selected from the group consisting of oxygen, nitrogen and sulfur. Saturated heterocyclic ring systems do not contain any double bond, whereas partially unsaturated heterocyclic ring systems contains at least one double bond, but do not form an aromatic system containing a heteroatom. The oxidized form of the ring nitrogen and sulfur atom contained in the heterocyclyl to provide the corresponding N-oxide, S-oxide or S,S-dioxide is also encompassed in the scope of the present invention. Representative examples of heterocyclyls include, but are not limited to, oxetane, azetidine, thietane, tetrahydrofuran, tetrahydrothiophene, pyrrolidine, dihydropyran, tetrahydropyran, thio-dihydropyran, thio-tetrahydropyran, piperidine, piperazine, morpholine, 1,3-oxazinane, 1,3-thiazinane, 4,5,6-tetrahydropyrimidine, 2,3-dihydrofuran, dihydrothiene, dihydropyridine, tetrahydropyridine, isoxazolidine and pyrazolidine.

Furthermore, unless stated otherwise, the heterocyclyl groups can be unsubstituted or substituted with one or more substituents independently selected from the group consisting of halogen, hydroxy, cyano, nitro, $-C(O)R_5$, $-C(O)$ $OR_5$, $-S(O)_tR_7$, $-NR_5R_6$, ($C_1$-$C_6$)alkyl, halo($C_1$-$C_6$)alkyl, $-O(C_1$-$C_6)$alkyl, halo($C_1$-$C_6$)alkoxy, ($C_3$-$C_8$)cycloalkyl, ($C_6$-$C_{10}$)aryl, heterocyclyl and heteroaryl; wherein $R_5$, $R_6$, $R_7$ and t are as defined above.

As used herein, the term "heteroaryl" refers to 5- to 10-membered monocyclic or bicyclic aromatic ring system containing one to four identical or different heteroatoms independently selected from the group consisting of oxygen, nitrogen and sulfur atom. For instance, the heteroaryl ring can be 5- to 8-membered monocyclic or bicyclic aromatic ring system or 5- to 6-membered monocyclic aromatic ring system or 5-membered monocyclic aromatic ring system or 6-membered monocyclic aromatic ring system. Representative examples of heteroaryl include, but are not limited to, furan, pyrrole, thiophene, imidazole, oxazole, thiazole, triazole, tetrazole, benzofuran, indole, benzoxazole, benzothiazole, isoxazole, triazine, purine, pyridine, pyrazine, quinoline, isoquinoline, phenazine, oxadiazole, pteridine, pyridazine, quinazoline, pyrimidine, isothiazole, quinoxaline (benzopyrazine), tetrazole and pyrido[2,3-b]pyrazine. The oxidized form of the ring nitrogen and sulfur atom contained in the heteroaryl to provide the corresponding N-oxide, S-oxide or S,S-dioxide is also encompassed in the scope of the present invention.

Furthermore, unless stated otherwise, the heteroaryl groups can be unsubstituted or substituted with one or more substituents, for example 1-4 substituents independently selected from the group consisting of halogen, hydroxy, cyano, nitro, $-C(O)R_5$, $-C(O)OR_5$, $-S(O)_tR_7$, $-NR_5R_6$, $-C(O)NR_5R_6$, $-S(O)_tNR_5R_6$, ($C_1$-$C_6$)alkyl, halo($C_1$-$C_6$) alkyl, $-O(C_1$-$C_6)$alkyl, halo($C_1$-$C_6$)alkoxy, ($C_3$-$C_8$)cycloalkyl, ($C_6$-$C_{10}$)aryl, heterocyclyl and heteroaryl; wherein $R_5$, $R_6$, $R_7$ and t are as defined above. Representative examples of heteroaryl include, but are not limited to, pyrrole, pyrazole, imidazole, isothiazole, pyrazine, furan, thiophene, triazole, benzothiazole, benzofuran, indole, purine, pyridine, quinoline, isoquinoline, pyridazine, quinazoline, pyrimidine and azocine.

The term "heteroatom" as used herein, includes nitrogen (N), oxygen (O) and sulfur (S). Any heteroatom with unsatisfied valency is assumed to have a hydrogen atom to satisfy the valency or when the heteroatom is N, it may be substituted with a group selected from the group consisting of $(C_1\text{-}C_6)$alkyl, —C(O)$(C_1\text{-}C_6)$alkyl, —C(O)O$(C_1\text{-}C_6)$alkyl and —S(O)$_2$$(C_1\text{-}C_6)$alkyl. Representative examples of $(C_1\text{-}C_6)$alkyl groups include, but are not limited to, methyl, ethyl, propyl, butyl, pentyl, hexyl, isopropyl and isobutyl.

As used herein, the term "isotopic forms" or "isotopically labelled forms" is a general term used for isotopic forms of the compounds of Formula (I), wherein one or more atoms of compounds of Formula (I) are replaced by their respective isotopes. All isotopes of any particular atom or element as specified are contemplated within the scope of the compounds of the invention. Examples of isotopes that can be incorporated into the compounds disclosed herein include, but are not limited to, isotopes of hydrogen such as $^2$H (deuterium or D) and $^3$H, carbon such as $^{11}$C, $^{13}$C and $^{14}$C, nitrogen such as $^{13}$N and $^{15}$N, oxygen such as $^{15}$O, $^{17}$O and $^{18}$O, chlorine such as $^{36}$Cl, fluorine such as $^{18}$F and sulfur such as $^{35}$S. Substitution with heavier isotopes, for example, replacing one or more key carbon-hydrogen bonds with carbon-deuterium bond may show certain therapeutic advantages, resulting from longer metabolism cycles (e.g., increased in vivo half life or reduced dosage requirements), improved safety or greater effectiveness and hence may be preferred in certain circumstances.

Representative examples of isotopic forms of the compounds of Formula (I) can include, without limitation, deuterated compounds of Formula (I). The term "deuterated" as used herein, by itself or used to modify a compound or group, refers to replacement of one or more hydrogen atom(s), which is attached to carbon(s), with a deuterium atom. For example, the compounds of Formula (I) can include in the definitions of one or more of the various variables $R_1$, $R_4$, $R_5$, $R_6$ and $R_7$ wherever applicable, deuterium, deuterated-alkyl, deuterated-alkoxy, deuterated-cycloalkyl, deuterated-heterocyclyl, deuterated-aryl, deuterated-heteroaryl and the like.

Within the context of the present invention and as used herein, the term "stereoisomer" is a general term used for all isomers of individual compounds that differ only in the orientation of their atoms in space. The term stereoisomer includes mirror image isomers (enantiomers), mixtures of mirror image isomers (racemates, racemic mixtures), geometric (cis/trans, syn/anti or E/Z) isomers, and isomers of compounds with more than one chiral center that are not mirror images of one another (diastereoisomers).

As used herein, the term "tautomer" refers to the coexistence of two or more compounds that differ from each other only in the position of one (or more) mobile atoms and in electron distribution. For example, proton tautomers (also known as prototropic tautomers) include interconversions via migration of a proton, such as keto-enol and imine-enamine tautomers.

The term "pharmaceutically acceptable salt(s)" as used herein includes a salt or salts of the active compounds i.e. the compounds of Formula (I) and are prepared with suitable acids or bases, depending on the particular substituents found on the compounds described herein.

As used herein, the term "solvate" or "solvates" describe a complex wherein the compound of Formula (I) of the present invention, is coordinated with a proportional amount of a solvent molecule. Specific solvates, wherein the solvent is water, are referred to as hydrates.

As used herein, the term "prodrug" refers to a compound that is drug precursor, which, when administered to a subject undergoes transformation through metabolic process or chemical transformation in vivo to form an active compound, for example, a prodrug after being brought to the physiological pH or through enzyme action is converted to active compounds, that is, compound of Formula (I) of the present invention. In context of the present invention prodrugs can be esters of the compound of Formula (I), which on metabolism can form an active compound of Formula (I).

As used herein, the term "polymorph" or "polymorphic form" or "polymorphs" refer to crystals of the same compound that differs only in the arrangement and/or conformation of the molecule in the crystal lattice.

As used herein, the term "N-oxide" refers to the oxide of the nitrogen atom of a nitrogen-containing heteroaryl or heterocycle. N-oxide can be formed in the presence of an oxidizing agent for example peroxide such as m-chloro-perbenzoic acid or hydrogen peroxide. N-oxide refers to an amine oxide, also known as amine-N-oxide, and is a chemical compound that contains N→O bond.

As used herein, the term "S-oxide" refers to the oxide of the sulfur atom (S-oxide) or dioxide of the sulfur atom (S,S-dioxide) of a sulfur-containing heteroaryl or heterocycle. S-oxide and S,S-dioxides can be formed in the presence of an oxidizing agent for example peroxide such as m-chloro-perbenzoic acid or oxone.

As used herein, the term "carboxylic acid isostere" refers to a functional group or a moiety that elicits similar physical, biological and/or chemical properties as a carboxylic acid moiety. Representative examples of carboxylic acid isostere include, but are not limited to:

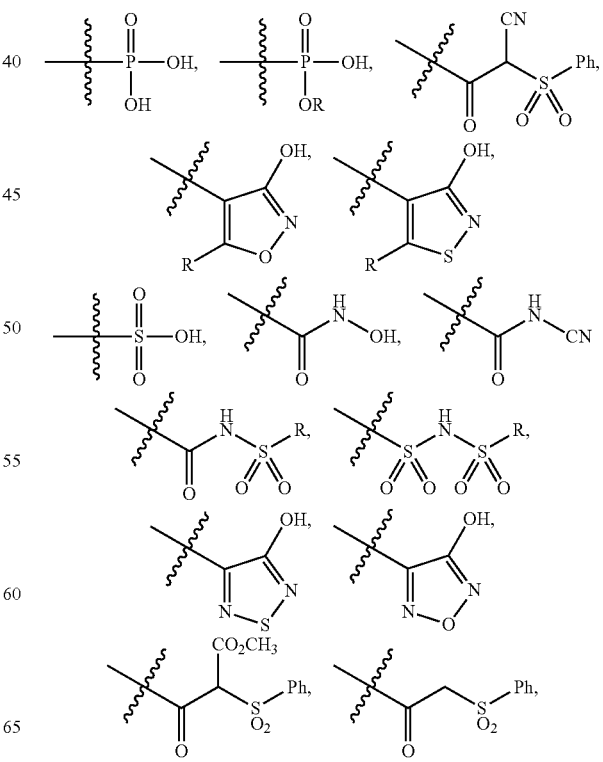

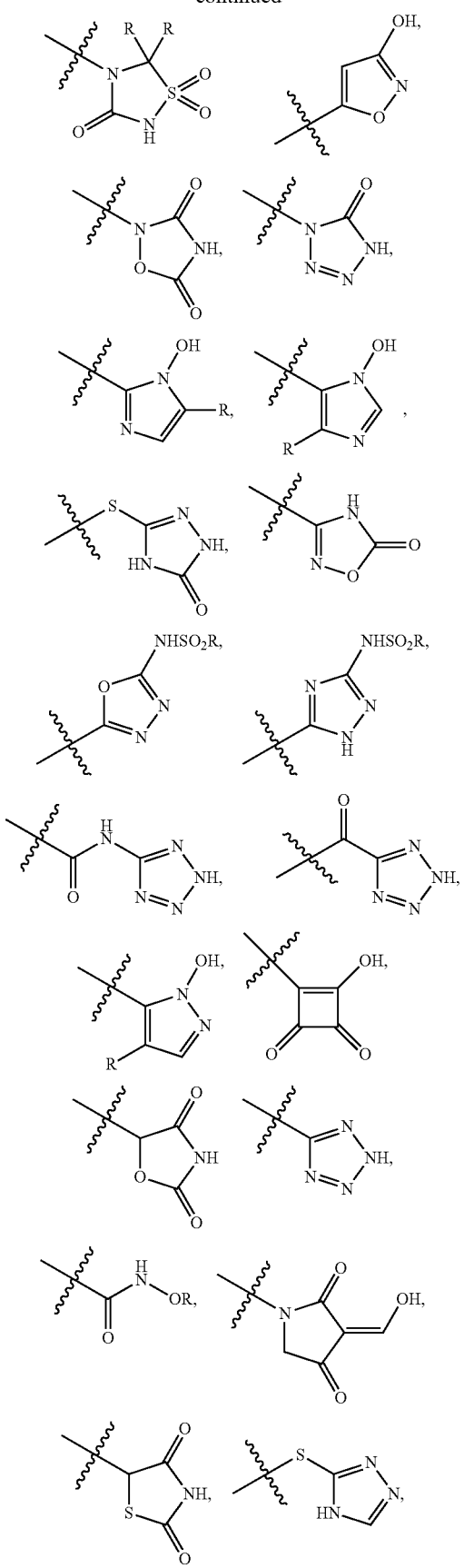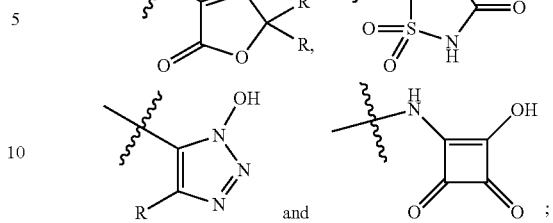

wherein R is hydrogen or $(C_1-C_3)$alkyl.

As used herein, the term "pharmaceutically acceptable" means that the carrier, diluent, excipient, and/or salt must be compatible with the other ingredients of the formulation, and not deleterious to the recipient thereof.

As used herein, the term "a disease or a disorder mediated by GPR120" or "GPR120 mediated disease(s) or disorder(s)" refers to a disease or a disorder or a condition characterized by inappropriate, for example, less than or greater than normal, GPR120 activity. A GPR120-mediated disease or disorder may be completely or partially mediated by inappropriate GPR120 activity.

The term "metabolic disorder" as used herein refers to a disorder relating to abnormality of metabolism. Accordingly, in the context of the present invention all the disorders relating to abnormality of metabolism are encompassed in the term "metabolic disorders".

The term "metabolic syndrome" refers to a cluster of metabolic abnormalities including abdominal obesity, insulin resistance, glucose intolerance, diabetes, hypertension and dyslipidemia. These abnormalities are known to be associated with an increased risk of vascular events.

The term "diabetes mellitus" or "diabetes" refers to a chronic disease or disorder, which occurs when the pancreas does not produce enough insulin, or when the body cannot effectively use the insulin it produces. This leads to an increased concentration of glucose in the blood (hyperglycaemia). Two major forms of diabetes are Type 1 diabetes (Insulin-dependent diabetes mellitus) and Type 2 diabetes (Non-insulin dependent diabetes mellitus (NIDDM)). Type 1 diabetes is an autoimmune disease in which the insulin-producing β-cells of the pancreas are destroyed which generally results in an absolute deficiency of insulin, the hormone that regulates glucose utilization. Type 2 diabetes often occurs in the face of normal or even elevated levels of insulin and can result from the inability of tissues to respond appropriately to insulin. Other categories of diabetes include gestational diabetes (a state of hyperglycemia which develops during pregnancy) and "other" rarer causes (genetic syndromes, acquired processes such as pancreatitis, diseases such as cystic fibrosis, exposure to certain drugs, viruses and unknown causes).

The term "cardiovascular disease" as used herein refers to any disease of the heart or blood vessels. One or more diseases of heart encompassed in the term "cardiovascular disease" is selected from, but are not limited to, angina, arrhythmia, coronary artery disease (CAD), cardiomyopathy, myocardial infarction, heart failure, hypertrophic cardiomyopathy, mitral regurgitation, mitral valve prolapse, pulmonary stenosis, etc. The blood vessel disease encompassed in the term "cardiovascular diseases", is selected from, but are not limited to, peripheral vascular disease, artery disease, carotid artery disease, deep vein thrombosis, venous diseases, atherosclerosis and the like.

The term "subject" as used herein refers to an animal, preferably a mammal, and most preferably a human. The term "mammal" as used herein refers to warm-blooded vertebrate animals of the class 'mammalia', including humans, characterized by a covering of hair on the skin and, in the female, milk-producing mammary glands for nourishing the young. The term mammal includes animals such as cat, dog, rabbit, bear, fox, wolf, monkey, deer, mouse, pig and human. In the context of the present invention the phrase "a subject in need thereof" means a subject (patient) in need of the treatment for the disease or disorder that is mediated by GPR120. Alternatively, the phrase "a subject in need thereof" means a subject (patient) diagnosed having a disease or a disorder that is mediated by GPR120. As used herein, the terms "treatment", "treat" and "therapy" refer to alleviate, slow the progression, attenuation, or cure of existing diseases or disorders (e.g. diabetes). Treatment also includes curing, preventing development of or alleviating to some extent, one or more of the symptoms of the diseases or disorders.

As used herein, the term "prophylaxis", used interchangeably with the terms "prevention" or "preventing" means preventing or reducing the probability of the occurrence of a clinical disease-state. Subjects are selected for preventative therapy based on factors that are known to increase risk of suffering a clinical disease state or a disorder compared to the general population. "Prophylaxis" therapies can be divided into (a) primary prevention and (b) secondary prevention. Primary prevention is defined as treatment in a subject that has not yet presented with a clinical disease state or a disorder, whereas secondary prevention is defined as preventing a second occurrence of the same or similar clinical disease state.

The term "pharmaceutically acceptable carrier" as used herein means a non-toxic, inert, solid, semi-solid, diluent, encapsulating material or formulation auxiliary of any type. Some examples of materials which can serve as pharmaceutically acceptable carriers are sugars such as lactose, glucose, and sucrose; starches such as corn starch and potato starch; cellulose and its derivatives such as sodium carboxymethyl cellulose, ethyl cellulose and cellulose acetate; malt; gelatin; talc; as well as other non-toxic compatible lubricants such as sodium lauryl sulfate and magnesium stearate, as well as coloring agents, releasing agents, coating agents, sweetening, flavoring and perfuming agents; preservatives and antioxidants can also be present in the composition, according to the judgment of the formulator.

The term "compound(s) for use" as used herein embrace any one or more of the following: (1) use of compound(s) of formula (I), (2) method of use of compound(s) of formula (I), (3) use of formula (I) in the treatment of, (4) the use of formula (I) for the manufacture of pharmaceutical composition/medicament for treatment/treating or (5) method of treatment/treating/preventing a disease or a disorder mediated by GPR120, comprising administering an effective amount of the compound of formula (I) to a subject in need thereof.

As used herein, the term, "therapeutically effective amount" refers to an amount of a compound of Formula (I) or a pharmaceutically acceptable salt thereof; or a composition comprising a compound of Formula (I) or a salt thereof, effective in producing the desired therapeutic response in a subject suffering from a disease or a disorder or a disorder mediated by GPR120. An example of a disease or disorder mediated by GPR120 is diabetes such as type 2 diabetes. Particularly, the term "therapeutically effective amount" includes the amount of a compound (in the context of the present invention, the compound of Formula (I) or a pharmaceutically acceptable salt thereof), when administered that induces a positive modification in the disease or disorder to be treated or is sufficient to prevent development of, or alleviate to some extent one or more of the symptoms of the disease or disorder being treated in a subject. In respect of the therapeutic amount of the compound, consideration is also given that the amount of the compound used for the treatment of a subject is low enough to avoid undue or severe side effects, within the scope of sound medical judgment. The therapeutically effective amount of the compound or composition will vary with the particular condition or disorder (in the context of the present invention, the disease or disorder that is mediated by GPR120) being treated, the age and physical condition of the subject, the severity of the condition or disorder being treated or prevented, the duration of the treatment, the nature of concurrent therapy, the specific compound or composition employed, the particular pharmaceutically acceptable carrier utilized and other related factors.

Within the context of the present invention and as used herein interchangeably throughout this application, the terms "compounds of Formula (I)" and "compounds of the present invention" include all the isotopic forms, stereoisomeric and tautomeric forms and mixtures thereof in all ratios, and their pharmaceutically acceptable salts, solvates, polymorphs, prodrugs, carboxylic acid isosteres, N-oxides and S-oxides. The compounds of Formula (I) are also referred to as fused heterocyclic compounds. Further, in the context of the present invention, reference to the compounds of Formula (I) includes reference to the compounds of Formula (Ia) and/or the compounds of one or more embodiments of the present invention as described herein. The compound(s) of the present invention can also be referred to herein as "the active compound(s)" or "the active ingredient(s)".

As used herein, the term "GPR120 agonist(s)" refer to the compound(s) which binds to, activates, increases, stimulates, potentiates, sensitizes or upregulates GPR120 receptor and promotes insulin sensitization. In the context of the present invention, the compounds of Formula (I) are provided for use as GPR120 agonists.

The term "optionally substituted" means "substituted or unsubstituted," and therefore, the generic structural formulae described herein encompass compounds that may or may not contain the specified optional substituent.

Embodiments

The invention encompasses all the compounds described by the Formula (I) without limitation, however, for the purposes of further illustrations, preferred aspects and elements of the invention are discussed herein in the form of the following embodiments.

In an embodiment, the present invention encompasses a compound of Formula (I), wherein $X_1$ is —O—.

In an embodiment, the present invention encompasses a compound of Formula (I), wherein $X_1$ is —S—.

In another embodiment, the present invention encompasses a compound of Formula (I), wherein $X_1$ is —NR'— and R' is as defined above.

In another embodiment, the present invention encompasses a compound of Formula (I), wherein $X_1$ is —NR'— and R' is selected from the group consisting of hydrogen, methyl, ethyl and propyl.

In another embodiment, the present invention encompasses a compound of Formula (I), wherein $X_2$ is —O— and "------" represents absence of bond.

In one embodiment, the present invention encompasses a compound of Formula (I), wherein $X_2$ is —S— and "------" represents absence of bond.

In another embodiment, the present invention encompasses a compound of Formula (I), wherein $X_2$ is —NR'—; R' is as defined above and "------" represents absence of bond.

In another embodiment, the present invention encompasses a compound of Formula (I), wherein $X_2$ is —NR'—; R' is selected from the group consisting of hydrogen, methyl, ethyl and propyl and "------" represents absence of bond.

In another embodiment, the present invention encompasses a compound of Formula (I), wherein $X_2$ is —CR'R"— and R' and R" are independently selected from the group consisting of hydrogen, $(C_1-C_6)$alkyl, —C(O)$(C_1-C_6)$alkyl, —C(O)O$(C_1-C_6)$alkyl, and —S(O)$_2$$(C_1-C_6)$alkyl; and "------" represents absence of bond.

In another embodiment, the present invention encompasses a compound of Formula (I), wherein $X_2$ is —CR'R"— and R' and R" are independently selected from the group consisting of hydrogen, methyl, ethyl and propyl; and "------" represents absence of bond.

In another embodiment, the present invention encompasses a compound of Formula (I), wherein $X_2$ is —CR'R"— and R' and R" are taken together to form oxo.

In another embodiment, the present invention encompasses a compound of Formula (I), wherein $X_2$ is —CR'R"— and R' and R" are taken together to form $(C_3-C_8)$cycloalkyl, $(C_5-C_8)$cycloalkenyl, or 3- to 6-membered saturated or a partially unsaturated heterocyclyl ring containing one or two heteroatoms independently selected from the group consisting of O, N and S and "------" represents absence of bond.

In another embodiment, the present invention encompasses a compound of Formula (I), wherein $X_2$ is —CR'R"— and R' and R" are taken together to form $(C_3-C_8)$cycloalkyl and "------" represents absence of bond.

In another embodiment, the present invention encompasses a compound of Formula (I), wherein $X_2$ is —CR'R"— and R' and R" are taken together to form cyclopropyl, cyclobutyl, cyclopentyl or cyclohexyl and "------" represents absence of bond.

In another embodiment, the present invention encompasses a compound of Formula (I), wherein $X_2$ is —CR'R"— and R' and R" are taken together to form cyclopropyl or cyclobutyl and "------" represents absence of bond.

In another embodiment, the present invention encompasses a compound of Formula (I), wherein $X_2$ is —CR'R"— and R' and R" are taken together to form a 3- to 6-membered saturated or a partially unsaturated heterocyclyl ring containing one or two heteroatoms independently selected from the group consisting of O, N and S and "------" represents absence of bond.

In another embodiment, the present invention encompasses a compound of Formula (I), wherein $X_2$ is —CR'R"— and R' and R" are taken together to form a 3- to 6-membered saturated or a partially unsaturated heterocyclyl ring containing an —O— atom.

In another embodiment, the present invention encompasses a compound of Formula (I), wherein $X_2$ is —CR'R"— and R' and R" are taken together to form a 3- to 6-membered saturated or a partially unsaturated heterocyclyl ring containing a —N— atom.

In another embodiment, the present invention encompasses a compound of Formula (I), wherein $X_2$ is —CR'R"— and R' and R" are taken together to form a 3- to 6-membered saturated or a partially unsaturated heterocyclyl ring containing a —S— atom.

In another embodiment, the present invention encompasses a compound of Formula (I), wherein $X_2$ is —CR'R"— and R' and R" are taken together to form a 3- or 4-membered saturated or a partially unsaturated heterocyclyl ring containing one heteroatom selected from the group consisting of O, N and S.

In another embodiment, the present invention encompasses a compound of Formula (I), wherein $X_2$ is —CR'R"— and R' and R" are taken together to form a saturated heterocyclyl ring selected from the group consisting of oxetane, thietane and azetidine; wherein said oxetane, thietane and azetidine can be optionally substituted.

In another embodiment, the present invention encompasses a compound of Formula (I), wherein $X_2$ is —CR'R"— and R' and R" are taken together to form azetidine, wherein the nitrogen of azetidine can be optionally substituted with $(C_1-C_6)$alkyl, —C(O)$(C_1-C_6)$alkyl, —C(O)O$(C_1-C_6)$alkyl or —S(O)$_2$$(C_1-C_6)$alkyl.

In another embodiment, the present invention encompasses a compound of Formula (I), wherein $X_2$ is —N—; and "------" represents a single bond.

In another embodiment, the present invention encompasses a compound of Formula (I), wherein $X_2$ is —CR'—; wherein R' is selected from the group consisting of hydrogen, methyl, ethyl and propyl and "------" represents a single bond.

In an embodiment, the present invention encompasses a compound of Formula (I), wherein $X_1$ is —O—, $X_2$ is —O— and "------" represents absence of bond.

In an embodiment, the present invention encompasses a compound of Formula (I), wherein $X_1$ is —O—, $X_2$ is —S— and "------" represents absence of bond.

In an embodiment, the present invention encompasses a compound of Formula (I), wherein $X_1$ is —O—, $X_2$ is —NR'—; wherein R' is selected from the group consisting of hydrogen, $(C_1-C_6)$alkyl, —C(O)$(C_1-C_6)$alkyl, —C(O)O$(C_1-C_6)$alkyl and —S(O)$_2$$(C_1-C_6)$alkyl; and "------" represents absence of bond.

In an embodiment, the present invention encompasses a compound of Formula (I), wherein $X_1$ is —O—, $X_2$ is —CR'R"—; wherein R' and R" are independently selected from the group consisting of hydrogen, $(C_1-C_6)$alkyl, —C(O)$(C_1-C_6)$alkyl, —C(O)O$(C_1-C_6)$alkyl and —S(O)$_2$$(C_1-C_6)$alkyl; and "------" represents absence of bond.

In an embodiment, the present invention encompasses a compound of Formula (I), wherein $X_1$ is —O—, $X_2$ is —CR'R"—; wherein R' and R" are taken together to form $(C_3-C_8)$cycloalkyl, $(C_5-C_8)$cycloalkenyl, or 3- to 6-membered saturated or a partially unsaturated heterocyclyl ring containing one or two heteroatoms independently selected from the group consisting of O, N and S and "------" represents absence of bond.

In an embodiment, the present invention encompasses a compound of Formula (I), wherein $X_1$ is —O—, $X_2$ is —CR'R"—; wherein R' and R" are taken together to form $(C_3-C_8)$cycloalkyl and "------" represents absence of bond.

In an embodiment, the present invention encompasses a compound of Formula (I), wherein $X_1$ is —O—, $X_2$ is —CR'R"—; wherein R' and R" are taken together to form cyclopropyl, cyclobutyl, cyclopentyl or cyclohexyl and "------" represents absence of bond.

In an embodiment, the present invention encompasses a compound of Formula (I), wherein $X_1$ is —O—, $X_2$ is —CR'R"—; wherein R' and R" are taken together to form cyclopropyl or cyclobutyl and "------" represents absence of bond.

In an embodiment, the present invention encompasses a compound of Formula (I), wherein $X_1$ is —O—, $X_2$ is —CR'R"—; wherein R' and R" are taken together to form a saturated or a partially unsaturated 3- to 6-membered heterocyclyl ring containing one or two heteroatoms independently selected from the group consisting of O, N and S and "------" represents absence of bond.

In an embodiment, the present invention encompasses a compound of Formula (I), wherein $X_1$ is —O—, $X_2$ is —CR'R"—; wherein R' and R" are taken together to form a 3- to 6-membered saturated or a partially unsaturated heterocyclyl ring containing an —O— atom.

In an embodiment, the present invention encompasses a compound of Formula (I), wherein $X_1$ is —O—, $X_2$ is —CR'R"—; wherein R' and R" are taken together to form a 3- to 6-membered saturated or a partially unsaturated heterocyclyl ring containing a —N— atom.

In an embodiment, the present invention encompasses a compound of Formula (I), wherein $X_1$ is —O—, $X_2$ is —CR'R"—; wherein R' and R" are taken together to form a 3- to 6-membered saturated or a partially unsaturated heterocyclyl ring containing a —S— atom.

In an embodiment, the present invention encompasses a compound of Formula (I), wherein $X_1$ is —O—, $X_2$ is —CR'R"—; wherein R' and R" are taken together to form a 3- or 4-membered saturated or a partially unsaturated heterocyclyl ring containing a heteroatom selected from a group consisting of O, N and S.

In an embodiment, the present invention encompasses a compound of Formula (I), wherein $X_1$ is —O—, $X_2$ is —CR'R"—; wherein R' and R" are taken together to form a saturated heterocyclyl ring selected from the group consisting of oxetane, thietane and azetidine, wherein said oxetane, thietane and azetidine can be optionally substituted.

In an embodiment, the present invention encompasses a compound of Formula (I), wherein $X_1$ is —O—, $X_2$ is —CR'R"—; wherein R' and R" are taken together to form azetidine; wherein the nitrogen of azetidine can be optionally substituted with $(C_1-C_6)$alkyl, —C(O)$(C_1-C_6)$alkyl, —C(O)O$(C_1-C_6)$alkyl or —S(O)$_2$$(C_1-C_6)$alkyl.

In an embodiment, the present invention encompasses a compound of Formula (I), wherein $X_1$ is —O—, $X_2$ is —N—; and "------" represents a single bond.

In an embodiment, the present invention encompasses a compound of Formula (I), wherein $X_1$ is —O—, $X_2$ is —CR'—; wherein R' is selected from the group consisting of hydrogen, $(C_1-C_6)$alkyl, —C(O)$(C_1-C_6)$alkyl, —C(O)O$(C_1-C_6)$alkyl and —S(O)$_2$$(C_1-C_6)$alkyl; and "------" represents a single bond.

In another embodiment, the present invention encompasses a compound of Formula (I), wherein ring A is $(C_6-C_{10})$aryl.

In another embodiment, the present invention encompasses a compound of Formula (I), wherein ring A is phenyl.

In another embodiment, the present invention encompasses a compound of Formula (I), wherein ring A is 5- to 10-membered heteroaryl.

In another embodiment, the present invention encompasses a compound of Formula (I), wherein ring A is a 5- to 8-membered monocyclic heteroaryl.

In another embodiment, the present invention encompasses a compound of Formula (I), wherein ring A is a 5- or 6-membered heteroaryl.

In another embodiment, the present invention encompasses a compound of Formula (I), wherein ring A is phenyl or 6-membered heteroaryl.

In another embodiment, the present invention encompasses a compound of Formula (I), wherein ring A is selected from the group consisting of phenyl, pyridyl, pyridazinyl, pyrimidinyl and pyrazinyl.

In another embodiment, the present invention encompasses a compound of Formula (I), wherein ring A is phenyl, $X_1$ is —O— and $X_2$ is —CR'—; wherein R' is selected from the group consisting of hydrogen, $(C_1-C_6)$alkyl, —C(O)$(C_1-C_6)$alkyl, —C(O)O$(C_1-C_6)$alkyl and —S(O)$_2$$(C_1-C_6)$alkyl; and "------" represents a single bond.

In another embodiment, the present invention encompasses a compound of Formula (I), wherein ring B is $(C_3-C_8)$cycloalkyl.

In another embodiment, the present invention encompasses a compound of Formula (I), wherein ring B is $(C_5-C_8)$cycloalkenyl.

In another embodiment, the present invention encompasses a compound of Formula (I), wherein ring B is cyclohexenyl.

In another embodiment, the present invention encompasses a compound of Formula (I), wherein ring B is $(C_6-C_{10})$aryl.

In another embodiment, the present invention encompasses a compound of Formula (I), wherein ring B is phenyl.

In another embodiment, the present invention encompasses a compound of Formula (I), wherein ring B is 5- to 10-membered heteroaryl.

In another embodiment, the present invention encompasses a compound of Formula (I), wherein ring B is 5- or 6-membered heteroaryl.

In another embodiment, the present invention encompasses a compound of Formula (I), wherein ring B is saturated or partially unsaturated 3- to 11-membered heterocyclyl ring.

In another embodiment, the present invention encompasses a compound of Formula (I), wherein ring B is saturated 3- to 11-membered heterocyclyl ring.

In another embodiment, the present invention encompasses a compound of Formula (I), wherein ring B is saturated 3- to 7-membered heterocyclyl ring.

In another embodiment, the present invention encompasses a compound of Formula (I), wherein ring B is partially unsaturated 3- to 9-membered heterocyclyl ring.

In another embodiment, the present invention encompasses a compound of Formula (I), wherein ring B is partially unsaturated 5- to 11-membered heterocyclyl ring.

In another embodiment, the present invention encompasses a compound of Formula (I), wherein ring B is partially unsaturated 5- to 11-membered heterocyclyl ring, wherein the ring is a bicyclic ring.

In another embodiment, the present invention encompasses a compound of Formula (I), wherein ring B is

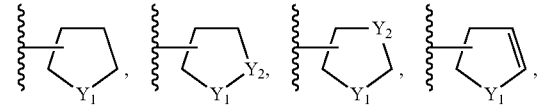

-continued

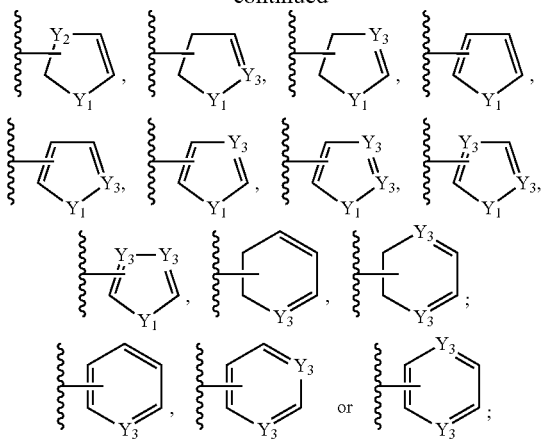

wherein $Y_1$ is —O—, —S— or —$NR_x$; $Y_2$ at each occurrence is independently selected from a group consisting of —O—, —S—, —NH—, —N($C_1$-$C_6$)alkyl and —C($R_y$)$_2$; $Y_3$ at each occurrence is independently selected from —N— or —$CR_y$; wherein $R_x$ is hydrogen, ($C_1$-$C_6$)alkyl, —C(O)($C_1$-$C_6$)alkyl, —C(O)O($C_1$-$C_6$)alkyl or —S(O)$_2$($C_1$-$C_6$)alkyl; $R_y$ at each occurrence is independently selected from the group consisting of hydrogen, halogen, oxo, cyano, nitro, —$NR_5R_6$, —C(O)$R_5$, —C(O)$NR_5R_6$, —S(O)$_tR_7$, ($C_1$-$C_6$)alkyl, halo($C_1$-$C_6$)alkyl, hydroxy, —O($C_1$-$C_6$)alkyl, —($C_3$-$C_6$)cycloalkyl, ($C_6$-$C_{10}$)aryl, —O($C_1$-$C_6$)aryl, heterocyclyl and heteroaryl.

In another embodiment, the present invention encompasses a compound of Formula (I), wherein ring B is

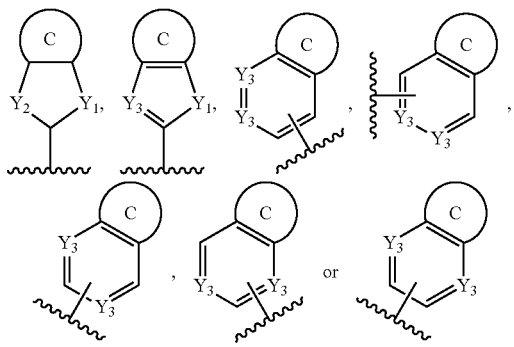

wherein ring C is selected from the group consisting of ($C_3$-$C_6$)cycloalkyl, ($C_6$-$C_{10}$)aryl, 5- or 6-membered heteroaryl and 5- or 6-membered heterocyclyl ring containing one or two heteroatoms independently selected from the group consisting of O, N and S; and $Y_1$, $Y_2$ and $Y_3$ are as defined above.

In another embodiment, the present invention encompasses a compound of Formula (I), wherein ring A is phenyl or 6-membered heteroaryl; and Ring B is

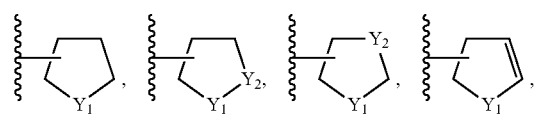

wherein $Y_2$ at each occurrence is independently selected from a group consisting of —O—, —S—, —NH—, —N($C_1$-$C_6$)alkyl and —C($R_y$)$_2$; $Y_1$, $Y_3$ and $R_y$ are as defined above.

In another embodiment, the present invention encompasses a compound of Formula (I), wherein ring A is phenyl or 6-membered heteroaryl and Ring B is

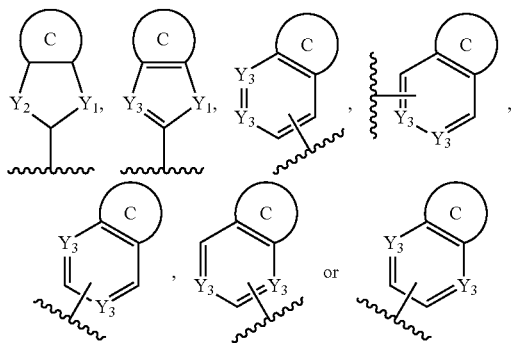

wherein ring C is selected from the group consisting of ($C_3$-$C_6$)cycloalkyl, ($C_6$-$C_{10}$)aryl, 5- or 6-membered heteroaryl and 5- or 6-membered heterocyclyl ring containing one or two heteroatoms independently selected from the group consisting of O, N and S; and $Y_1$, $Y_2$ and $Y_3$ are as defined above.

In another embodiment, the present invention encompasses a compound of Formula (I), wherein $R_2$ is hydrogen.

In another embodiment, the present invention encompasses a compound of Formula (I), wherein $R_a$ and $R_b$ are hydrogen and n is as defined above.

In an embodiment, the present invention encompasses a compound of Formula (I), wherein n is 2, 3 or 4.

In another embodiment, the present invention encompasses a compound of Formula (I), wherein n is 3.

In an embodiment, the present invention encompasses a compound of Formula (I), wherein $R_3$ is halogen.

In an embodiment, the present invention encompasses a compound of Formula (I), wherein $R_3$ is F, Cl or Br.

In another embodiment, the present invention encompasses a compound of Formula (I), wherein $R_3$ is F.

In another embodiment, the compound of Formula (I) encompasses a compound of Formula (Ia);

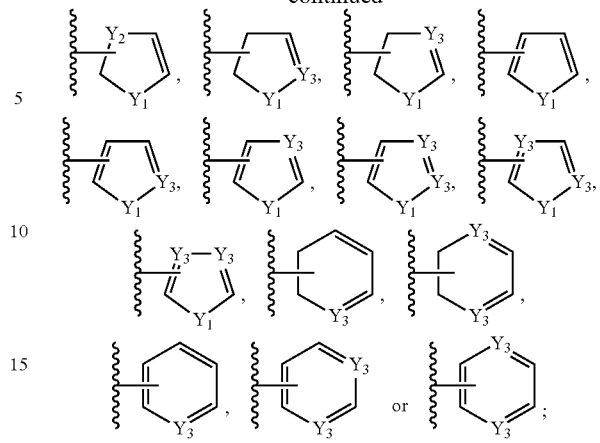

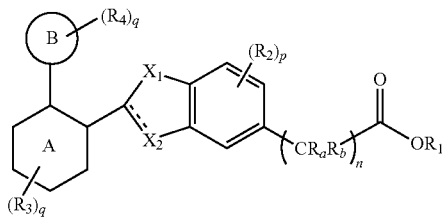

Formula (Ia)

Wherein, $X_1$ is —O—, —S— or —NR';

$X_2$ is —O—, —S—, —N—, —NR'—, —CR'— or —CR'R"—;

Ring A is phenyl or 6-membered heteroaryl;

Ring B is $(C_3-C_8)$cycloalkyl, $(C_5-C_8)$cycloalkenyl, $(C_6-C_{10})$aryl, 5- to 10-membered heteroaryl or a saturated or partially unsaturated 3- to 11-membered heterocyclyl ring containing one to four heteroatoms independently selected from the group consisting of O, N and S;

$R_1$ is hydrogen or $(C_1-C_6)$alkyl;

$R_2$ at each occurrence is independently selected from the group consisting of hydrogen, halogen, hydroxy, cyano, nitro, —$NR_5R_6$, —$C(O)R_5$, —$C(O)NR_5R_6$, —$S(O)_tR_7$, $(C_1-C_6)$alkyl, halo$(C_1-C_6)$alkyl, —$O(C_1-C_6)$alkyl and $(C_6-C_{10})$aryl;

$R_3$ at each occurrence is independently selected from the group consisting of hydrogen, halogen, oxo, cyano, nitro, —$NR_5R_6$, —$C(O)R_5$, —$C(O)NR_5R_6$, —$S(O)_tR_7$, $(C_1-C_6)$alkyl, halo$(C_1-C_6)$alkyl, hydroxy and —$O(C_1-C_6)$alkyl;

$R_4$ at each occurrence is independently selected from the group consisting of hydrogen, halogen, oxo, cyano, nitro, —$NR_5R_6$, —$C(O)R_5$, —$C(O)NR_5R_6$, —$S(O)_tR_7$, $(C_1-C_6)$alkyl, halo$(C_1-C_6)$alkyl, hydroxy, —$O(C_1-C_6)$alkyl, $(C_3-C_8)$cycloalkyl, $(C_6-C_{10})$aryl, —$O(C_1-C_6)$aryl, heterocyclyl and heteroaryl;

$R_5$ and $R_6$ at each occurrence are independently selected from the group consisting of hydrogen, $(C_1-C_6)$alkyl, $(C_6-C_{10})$aryl, heterocyclyl and heteroaryl;

$R_7$ is hydrogen, $(C_1-C_6)$alkyl or —$NR_5R_6$;

R' and R" at each occurrence are independently selected from the group consisting of hydrogen, $(C_1-C_6)$alkyl, —$C(O)(C_1-C_6)$alkyl, —$C(O)O(C_1-C_6)$alkyl and —$S(O)_2(C_1-C_6)$alkyl; or R' and R" are taken together to form oxo, $(C_3-C_8)$cycloalkyl, $(C_5-C_8)$cycloalkenyl, or 3- to 6-membered saturated or a partially unsaturated heterocyclyl ring containing one or two heteroatoms independently selected from the group consisting of O, N and S;

$R_a$ and $R_b$ at each occurrence are independently selected from the group consisting of hydrogen, halogen and $(C_1-C_6)$alkyl;

n is an integer from 1 to 6;

p is an integer from 1 to 3;

q is an integer from 1 to 4;

t is an integer from 0 to 2;

------- represents presence or absence of a single bond;

wherein, $(C_1-C_6)$alkyl is unsubstituted or substituted with one or more groups independently selected from the group consisting of halogen, hydroxy, cyano, nitro, —$NR_5R_6$, —$C(O)R_5$, —$C(O)NR_5R_6$, —$S(O)_tR_7$, $(C_1-C_6)$alkyl, halo$(C_1-C_6)$alkyl, —$O(C_1-C_6)$alkyl, $(C_3-C_8)$cycloalkyl, $(C_6-C_{10})$aryl, heterocyclyl and heteroaryl; wherein $R_5$, $R_6$, $R_7$ and t are as defined above;

—$O(C_1-C_6)$alkyl is unsubstituted or substituted with one or more groups independently selected from the group consisting of halogen, hydroxy, cyano, nitro, —$NR_5R_6$, —$C(O)R_5$, —$C(O)NR_5R_6$, —$S(O)_tR_7$, $(C_1-C_6)$alkyl, halo$(C_1-C_6)$alkyl, $(C_6-C_{10})$aryl, $(C_3-C_8)$cycloalkyl, and heterocyclyl; wherein $R_5$, $R_6$, $R_7$ and t are as defined above;

$(C_3-C_8)$cycloalkyl is unsubstituted or substituted with one or more groups independently selected from the group consisting of oxo, halogen, hydroxy, cyano, nitro, —$NR_5R_6$, —$C(O)R_5$, —$C(O)NR_5R_6$, —$S(O)_tR_7$, $(C_1-C_6)$alkyl, halo$(C_1-C_6)$alkyl and —$O(C_1-C_6)$alkyl; wherein $R_5$, $R_6$, $R_7$ and t are as defined above;

$(C_5-C_8)$cycloalkenyl is unsubstituted or substituted with one or more groups independently selected from the group consisting of halogen, hydroxy, cyano, nitro, —$NR_5R_6$, —$C(O)R_5$, —$C(O)NR_5R_6$, —$S(O)_tR_7$, $(C_1-C_6)$alkyl, halo$(C_1-C_6)$alkyl and —$O(C_1-C_6)$alkyl; wherein $R_5$, $R_6$, $R_7$ and t are as defined above;

$(C_6-C_{10})$aryl is unsubstituted or substituted with one or more groups independently selected from the group consisting of halogen, hydroxy, cyano, nitro, —$C(O)R_5$, —$C(O)OR_5$, —$S(O)_tR_7$, —$NR_5R_6$, $(C_1-C_6)$alkyl, halo$(C_1-C_6)$alkyl, —$O(C_1-C_6)$alkyl, halo$(C_1-C_6)$alkoxy, $(C_3-C_8)$cycloalkyl, $(C_6-C_{10})$aryl, —$O(C_6-C_{10})$aryl, heterocyclyl and heteroaryl, wherein $R_5$, $R_6$, $R_7$ and t are as defined above;

heterocyclyl is a 3- to 11-membered ring, which is unsubstituted or substituted with one or more groups independently selected from the group consisting of halogen, hydroxy, cyano, nitro, —$C(O)R_5$, —$C(O)OR_5$, —$S(O)_tR_7$, —$NR_5R_6$, $(C_1-C_6)$alkyl, halo$(C_1-C_6)$alkyl, —$O(C_1-C_6)$alkyl, halo$(C_1-C_6)$alkoxy, $(C_3-C_6)$cycloalkyl, $(C_6-C_{10})$aryl, heterocyclyl and heteroaryl; wherein $R_5$, $R_6$, $R_7$ and t are as defined above;

heteroaryl is a 5- to 10-membered ring, which is unsubstituted or substituted with one or more groups independently selected from the group consisting of halogen, hydroxy, cyano, nitro, —$C(O)R_5$, —$C(O)OR_5$, —$S(O)_tR_7$, —$NR_5R_6$, $(C_1-C_6)$alkyl, halo$(C_1-C_6)$alkyl, —$O(C_1-C_6)$alkyl, halo$(C_1-C_6)$alkoxy, $(C_3-C_8)$cycloalkyl, $(C_6-C_{10})$aryl, heterocyclyl and heteroaryl; wherein $R_5$, $R_6$, $R_7$ and t are as defined above;

halogen is chlorine, bromine, iodine or fluorine; or an isotopic form, a stereoisomer, a tautomer, a pharmaceutically acceptable salt, a pharmaceutically acceptable solvate, a prodrug, a polymorph, N-oxide, S-oxide, or a carboxylic acid isostere thereof.

In an embodiment, the compound of Formula (I) encompasses a compound of Formula (Ia); wherein $X_1$ is —O—.

In an embodiment, the compound of Formula (I) encompasses a compound of Formula (Ia); wherein $X_1$ is —S—.

In an embodiment, the compound of Formula (I) encompasses a compound of Formula (Ia); wherein $X_1$ is —NR'— and R' is as defined above.

In an embodiment, the compound of Formula (I) encompasses a compound of Formula (Ia); wherein $X_1$ is —NR'— and R' is selected from the group consisting of hydrogen, methyl, ethyl and propyl.

In an embodiment, the compound of Formula (I) encompasses a compound of Formula (Ia); wherein $X_2$ is —O— and "-------" represents absence of bond.

In an embodiment, the compound of Formula (I) encompasses a compound of Formula (Ia); wherein $X_2$ is —S— and "-------" represents absence of bond.

In another embodiment, the compound of Formula (I) encompasses a compound of Formula (Ia); wherein $X_2$ is —NR'—; R' is as defined above and "-------" represents absence of bond.

In another embodiment, the compound of Formula (I) encompasses a compound of Formula (Ia); wherein $X_2$ is —NR'—; R' is selected from the group consisting of hydrogen, methyl, ethyl and propyl and "------" represents absence of bond.

In another embodiment, the compound of Formula (I) encompasses a compound of Formula (Ia); wherein $X_2$ is —CR'R"— and R' and R" are independently selected from the group consisting of hydrogen, $(C_1-C_6)$alkyl, —C(O)($C_1$-$C_6$)alkyl, —C(O)O($C_1$-$C_6$)alkyl, and —S(O)$_2$($C_1$-$C_6$)alkyl; and "------" represents absence of bond.

In another embodiment, the compound of Formula (I) encompasses a compound of Formula (Ia); wherein $X_2$ is —CR'R"— and R' and R" are independently selected from the group consisting of hydrogen, methyl, ethyl and propyl; and "------" represents absence of bond.

In another embodiment, the compound of Formula (I) encompasses a compound of Formula (Ia); wherein $X_2$ is —CR'R"— and R' and R" are taken together to form oxo.

In another embodiment, the compound of Formula (I) encompasses a compound of Formula (Ia); wherein $X_2$ is —CR'R"— and R' and R" are taken together to form $(C_3-C_8)$cycloalkyl, $(C_5-C_8)$cycloalkenyl, or 3- to 6-membered saturated or a partially unsaturated heterocyclyl ring containing one or two heteroatoms independently selected from the group consisting of O, N and S and "------" represents absence of bond.

In another embodiment, the compound of Formula (I) encompasses a compound of Formula (Ia); wherein $X_2$ is —CR'R"— and R' and R" are taken together to form $(C_3-C_8)$cycloalkyl and "------" represents absence of bond.

In another embodiment, the compound of Formula (I) encompasses a compound of Formula (Ia); wherein $X_2$ is —CR'R"— and R' and R" are taken together to form cyclopropyl, cyclobutyl, cyclopentyl or cyclohexyl and "------" represents absence of bond.

In another embodiment, the compound of Formula (I) encompasses a compound of Formula (Ia); wherein $X_2$ is —CR'R"— and R' and R" are taken together to form cyclopropyl or cyclobutyl and "------" represents absence of bond.

In another embodiment, the compound of Formula (I) encompasses a compound of Formula (Ia); wherein $X_2$ is —CR'R"— and R' and R" are taken together to form a 3- to 6-membered saturated or a partially unsaturated heterocyclyl ring containing one or two heteroatoms independently selected from the group consisting of O, N and S and "------" represents absence of bond.

In another embodiment, the compound of Formula (I) encompasses a compound of Formula (Ia); wherein $X_2$ is —CR'R"— and R' and R" are taken together to form a 3- to 6-membered saturated or a partially unsaturated heterocyclyl ring containing an —O— atom.

In another embodiment, the compound of Formula (I) encompasses a compound of Formula (Ia); wherein $X_2$ is —CR'R"— and R' and R" are taken together to form a 3- to 6-membered saturated or a partially unsaturated heterocyclyl ring containing a —N— atom.

In another embodiment, the compound of Formula (I) encompasses a compound of Formula (Ia); wherein $X_2$ is —CR'R"— and R' and R" are taken together to form a 3- to 6-membered saturated or a partially unsaturated heterocyclyl ring containing a —S— atom.

In another embodiment, the compound of Formula (I) encompasses a compound of Formula (Ia); wherein $X_2$ is —CR'R"— and R' and R" are taken together to form a 3- or 4-membered saturated or a partially unsaturated heterocyclyl ring containing one heteroatom selected from the group consisting of O, N and S.

In another embodiment, the compound of Formula (I) encompasses a compound of Formula (Ia); wherein $X_2$ is —CR'R"— and R' and R" are taken together to form a saturated heterocyclyl ring selected from the group consisting of oxetane, thietane and azetidine, wherein said oxetane, thietane and azetidine can be optionally substituted.

In another embodiment, the compound of Formula (I) encompasses a compound of Formula (Ia); wherein $X_2$ is —CR'R"— and R' and R" are taken together to form azetidine, wherein the nitrogen of azetidine can be optionally substituted with ($C_1$-$C_6$alkyl), —C(O)($C_1$-$C_6$alkyl), —C(O)O($C_1$-$C_6$alkyl) or —S(O)$_2$($C_1$-$C_6$alkyl).

In another embodiment, the compound of Formula (I) encompasses a compound of Formula (Ia); wherein $X_2$ is —N—; and "------" represents a single bond.

In another embodiment, the compound of Formula (I) encompasses a compound of Formula (Ia); wherein $X_2$ is —CR'—; wherein R' is selected from the group consisting of hydrogen, methyl, ethyl and propyl and "------" represents a single bond.

In an embodiment, the compound of Formula (I) encompasses a compound of Formula (Ia); wherein $X_1$ is —O—, $X_2$ is —NR'—; wherein R' is selected from the group consisting of hydrogen, $(C_1-C_6)$alkyl, —C(O)($C_1$-$C_6$)alkyl, —C(O)O($C_1$-$C_6$)alkyl and —S(O)$_2$($C_1$-$C_6$)alkyl; and "------" represents absence of bond.

In another embodiment, the compound of Formula (I) encompasses a compound of Formula (Ia); wherein $X_1$ is —O—, $X_2$ is —CR'R"—; wherein R' and R" are independently selected from the group consisting of hydrogen, $(C_1-C_6)$alkyl, —C(O)($C_1$-$C_6$)alkyl, —C(O)O($C_1$-$C_6$)alkyl and —S(O)$_2$($C_1$-$C_6$)alkyl; and "------" represents absence of bond.

In an embodiment, the compound of Formula (I) encompasses a compound of Formula (Ia); wherein $X_1$ is —O—, $X_2$ is —CR'R"—; wherein R' and R" are taken together to form $(C_3-C_8)$cycloalkyl, $(C_5-C_8)$cycloalkenyl, or 3- to 6-membered saturated or a partially unsaturated heterocyclyl ring containing one or two heteroatoms independently selected from the group consisting of O, N and S and "------" represents absence of bond.

In an embodiment, the compound of Formula (I) encompasses a compound of Formula (Ia); wherein $X_1$ is —O—, $X_2$ is —CR'R"—; wherein R' and R" are taken together to form $(C_3-C_8)$cycloalkyl and "------" represents absence of bond.

In an embodiment, the compound of Formula (I) encompasses a compound of Formula (Ia); wherein $X_1$ is —O—, $X_2$ is —CR'R"—; wherein R' and R" are taken together to form cyclopropyl, cyclobutyl, cyclopentyl or cyclohexyl and "------" represents absence of bond.

In an embodiment, the compound of Formula (I) encompasses a compound of Formula (Ia); wherein $X_1$ is —O—, $X_2$ is —CR'R"—; wherein R' and R" are taken together to form a 3- to 6-membered saturated or a partially unsaturated heterocyclyl ring containing one or two heteroatoms independently selected from the group consisting of O, N and S and "------" represents absence of bond.

In an embodiment, the compound of Formula (I) encompasses a compound of Formula (Ia); wherein $X_1$ is —O—, $X_2$ is —CR'R"—; wherein R' and R" are taken together to form a 3- to 6-membered saturated or a partially unsaturated heterocyclyl ring containing an —O— atom.

In an embodiment, the compound of Formula (I) encompasses a compound of Formula (Ia); wherein $X_1$ is —O—, $X_2$ is —CR'R"—; wherein R' and R" are taken together to form a 3- to 6-membered saturated or a partially unsaturated heterocyclyl ring containing a —N— atom.

In an embodiment, the compound of Formula (I) encompasses a compound of Formula (Ia); wherein $X_1$ is —O—, $X_2$ is —CR'R"—; wherein R' and R" are taken together to form 3- or 4-membered saturated or a partially unsaturated heterocyclyl ring containing a heteroatom selected from a group of O, N and S.

In an embodiment, the compound of Formula (I) encompasses a compound of Formula (Ia); wherein $X_1$ is —O—, $X_2$ is —CR'R"—; R' and R" are taken together to form a saturated heterocyclyl ring independently selected from the group consisting of oxetane, thietane and azetidine, wherein said oxetane, thietane and azetidine can be optionally substituted.

In an embodiment, the compound of Formula (I) encompasses a compound of Formula (Ia); wherein $X_1$ is —O—, $X_2$ is —CR'R"—; wherein R' and R" are taken together to form azetidine; wherein the nitrogen of azetidine can be optionally substituted with $(C_1-C_6)$alkyl, —C(O)$(C_1-C_6)$alkyl, —C(O)O$(C_1-C_6)$alkyl or —S(O)$_2$$(C_1-C_6)$alkyl.

In an embodiment, the compound of Formula (I) encompasses a compound of Formula (Ia); wherein $X_1$ is —O—, $X_2$ is —N—; and "------" represents a single bond.

In an embodiment, the compound of Formula (I) encompasses a compound of Formula (Ia); wherein $X_1$ is —O—, $X_2$ is —CR'—; wherein R' is selected from the group consisting of hydrogen, $(C_1-C_6)$alkyl, —C(O)$(C_1-C_6)$alkyl, —C(O)O$(C_1-C_6)$alkyl and —S(O)$_2$$(C_1-C_6)$alkyl; and "------" represents a single bond.

In another embodiment, the compound of Formula (I) encompasses a compound of Formula (Ia); wherein $R_4$ at each occurrence is independently selected from the group consisting of hydrogen, halogen, oxo, cyano, nitro, —NR$_5$R$_6$, —C(O)R$_5$, —C(O)NR$_5$R$_6$, —S(O)$_r$R$_7$, $(C_1-C_6)$alkyl, halo$(C_1-C_6)$alkyl, $(C_3-C_8)$cycloalkyl, hydroxy, —O$(C_1-C_6)$alkyl and —O$(C_1-C_6)$aryl.

In another embodiment, the compound of Formula (I) encompasses a compound of Formula (Ia); wherein ring A is phenyl ring.

In another embodiment, the compound of Formula (I) encompasses a compound of Formula (Ia); wherein ring A is 6-membered heteroaryl.

In another embodiment, the compound of Formula (I) encompasses a compound of Formula (Ia); wherein ring A is selected from the group consisting of pyridyl, pyridazinyl, pyrimidinyl and pyrazinyl.

In another embodiment, the compound of Formula (I) encompasses a compound of Formula (Ia); wherein ring A is 6-membered heteroaryl, $X_1$ is —O— and $X_2$ is —CR'—; wherein R' is selected from the group consisting of hydrogen, $(C_1-C_6)$alkyl, —C(O)$(C_1-C_6)$alkyl, —C(O)O$(C_1-C_6)$alkyl and —S(O)$_2$$(C_1-C_6)$alkyl; and "------" represents a single bond.

In another embodiment, the compound of Formula (I) encompasses a compound of Formula (Ia); wherein ring A is phenyl, $X_1$ is —O— and $X_2$ is —CR'—; wherein R' is selected from the group consisting of hydrogen, $(C_1-C_6)$alkyl, —C(O)$(C_1-C_6)$alkyl, —C(O)O$(C_1-C_6)$alkyl and —S(O)$_2$$(C_1-C_6)$alkyl; and "------" represents a single bond.

In another embodiment, the compound of Formula (I) encompasses a compound of Formula (Ia); wherein ring B phenyl.

In another embodiment, the compound of Formula (I) encompasses a compound of Formula (Ia); wherein ring B is 5- to 10-membered heteroaryl.

In another embodiment, the compound of Formula (I) encompasses a compound of Formula (Ia); wherein ring B is 5- or 6-membered heteroaryl.

In another embodiment, the compound of Formula (I) encompasses a compound of Formula (Ia); wherein ring B is saturated or partially unsaturated 3- to 11-membered heterocyclyl ring.

In another embodiment, the compound of Formula (I) encompasses a compound of Formula (Ia); wherein ring B is saturated 3- to 11-membered heterocyclyl ring.

In another embodiment, the compound of Formula (I) encompasses a compound of Formula (Ia); wherein ring B is saturated 3- to 7-membered heterocyclyl ring.

In another embodiment, the compound of Formula (I) encompasses a compound of Formula (Ia); wherein ring B is partially unsaturated 3- to 9-membered heterocyclyl ring.

In another embodiment, the present invention encompasses a compound of Formula (I), wherein ring B is partially unsaturated 5- to 11-membered heterocyclyl ring.

In another embodiment, the present invention encompasses a compound of Formula (I), wherein ring B is partially unsaturated 5- to 11-membered heterocyclyl ring, wherein the ring is a bicyclic ring.

In another embodiment, the compound of Formula (I) encompasses a compound of Formula (Ia); wherein ring B is

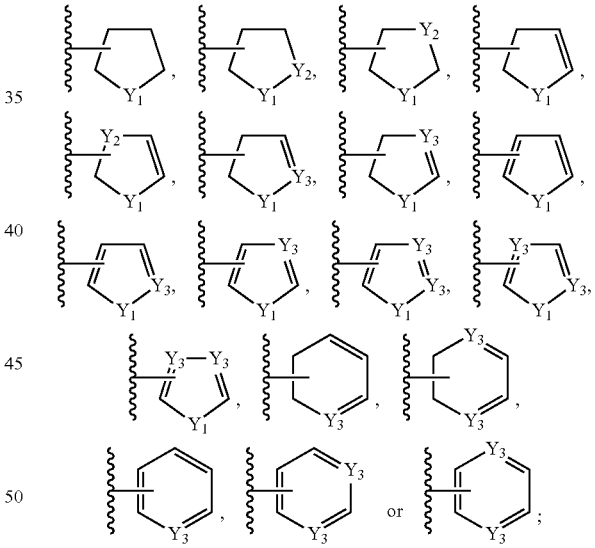

wherein $Y_1$ is —O—, —S— or —NR$_x$; $Y_2$ at each occurrence is independently selected from a group consisting of —O—, —S—, —NH—, —N$(C_1-C_6)$alkyl and —C(R$_y$)$_2$; $Y_3$ at each occurrence is independently selected from —N— or —CR$_y$; wherein R$_x$ is hydrogen, $(C_1-C_6)$alkyl, —C(O)$(C_1-C_6)$alkyl, —C(O)O$(C_1-C_6)$alkyl or —S(O)$_2$$(C_1-C_6)$alkyl; R$_y$ at each occurrence is independently selected from the group consisting of hydrogen, halogen, oxo, cyano, nitro, —NR$_5$R$_6$, —C(O)R$_5$, —C(O)NR$_5$R$_6$, —S(O)$_r$R$_7$, $(C_1-C_6)$alkyl, halo$(C_1-C_6)$alkyl, hydroxy, —O$(C_1-C_6)$alkyl, —$(C_3-C_8)$cycloalkyl, $(C_6-C_{10})$aryl, —O$(C_1-C_6)$aryl, heterocyclyl and heteroaryl.

In another embodiment, the compound of Formula (I) encompasses a compound of Formula (Ia); wherein ring B is

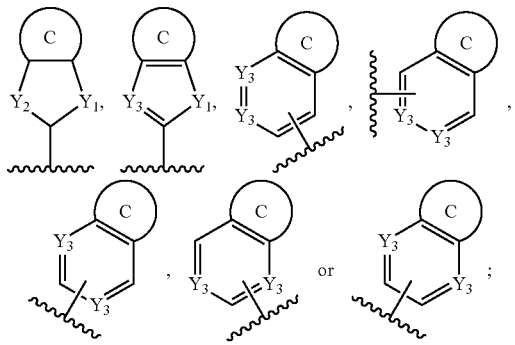

wherein ring C is selected from the group consisting of (C$_3$-C$_6$)cycloalkyl, (C$_6$-C$_{10}$)aryl, 5- or 6-membered heteroaryl and 5- or 6-membered heterocyclyl ring containing one or two heteroatoms independently selected from the group consisting of O, N and S; and Y$_1$, Y$_2$ and Y$_3$ are as defined above.

In another embodiment, the compound of Formula (I) encompasses a compound of Formula (Ia); wherein R$_2$, R$_a$ and R$_b$ are hydrogen.

In another embodiment, the compound of Formula (I) encompasses a compound of Formula (Ia); wherein ring A is phenyl or 6-membered heteroaryl and ring B is

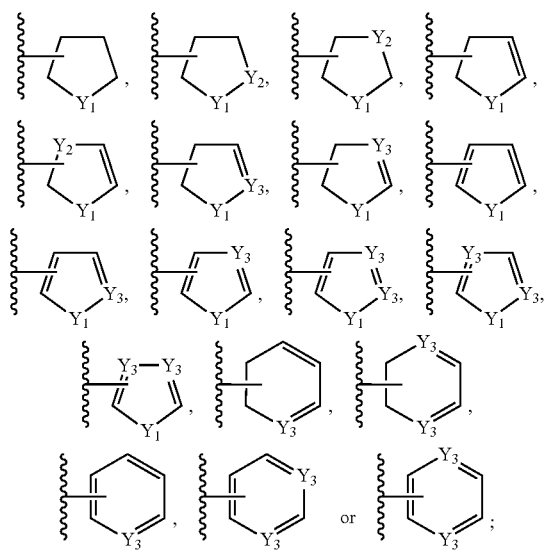

wherein Y$_1$ is —O—, —S— or —NR$_x$; Y$_2$ at each occurrence is independently selected from a group consisting of —O—, —S—, —NH—, —N(C$_1$-C$_6$)alkyl and —C(R$_y$)$_2$; Y$_3$ at each occurrence is independently selected from —N— or —CR$_y$; wherein R$_x$ is hydrogen, (C$_1$-C$_6$) alkyl, —C(O)(C$_1$-C$_6$)alkyl, —C(O)O(C$_1$-C$_6$)alkyl or —S(O)$_2$(C$_1$-C$_6$)alkyl; R$_y$ at each occurrence is independently selected from the group consisting of hydrogen, halogen, oxo, cyano, nitro, —NR$_5$R$_6$, —C(O)R$_5$, —C(O)NR$_5$R$_6$, —S(O)$_t$R$_7$, (C$_1$-C$_6$)alkyl, halo(C$_1$-C$_6$)alkyl, hydroxy, —O(C$_1$-C$_6$)alkyl, —(C$_3$-C$_8$)cycloalkyl, (C$_6$-C$_{10}$) aryl, —O(C$_1$-C$_6$)aryl, heterocyclyl and heteroaryl.

In another embodiment, the compound of Formula (I) encompasses a compound of Formula (Ia); wherein ring A is phenyl and ring B is

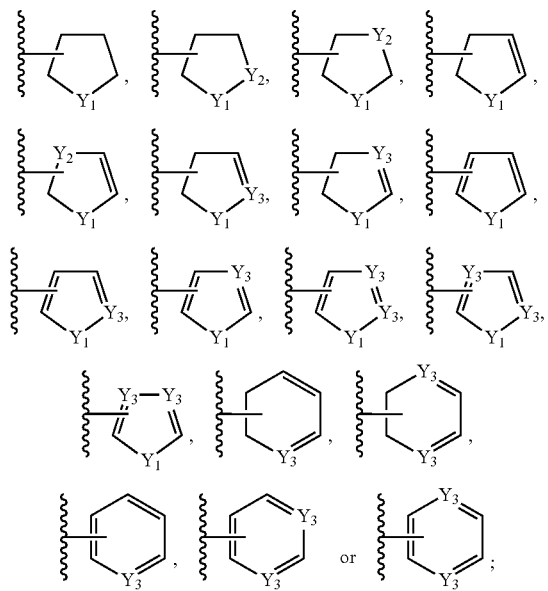

wherein Y$_1$, Y$_2$ and Y$_3$ are as defined above.

In another embodiment, the compound of Formula (I) encompasses a compound of Formula (Ia); wherein ring A is phenyl or 6-membered heteroaryl and ring B is

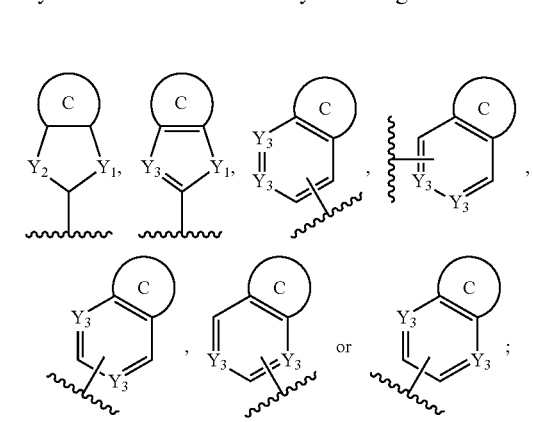

wherein ring C is selected from the group consisting of (C$_3$-C$_6$)cycloalkyl, (C$_6$-C$_{10}$)aryl, 5- or 6-membered heteroaryl and 5- or 6-membered heterocyclyl ring containing one or two heteroatoms independently selected from the group consisting of O, N and S; and Y$_1$, Y$_2$ and Y$_3$ are as defined above.

In another embodiment, the compound of Formula (I) encompasses a compound of Formula (Ia); wherein ring A is phenyl and ring B is

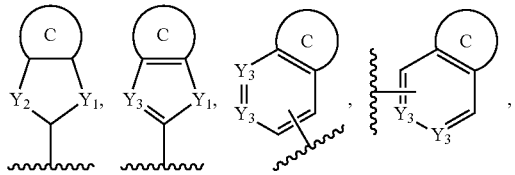

-continued

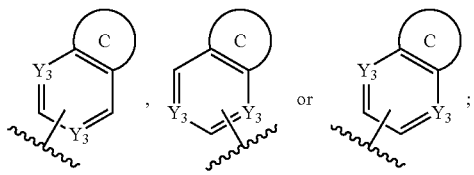

wherein ring C is selected from the group consisting of (C$_3$-C$_6$)cycloalkyl, (C$_6$-C$_{10}$)aryl, 5- or 6-membered heteroaryl and 5- or 6-membered heterocyclyl ring containing one or two heteroatoms independently selected from the group consisting of O, N and S; and Y$_1$, Y$_2$ and Y$_3$ are as defined above.

In another embodiment, the compound of Formula (I) encompasses a compound of Formula (Ia); wherein X$_1$ is —O— and X$_2$ is —CR'—; wherein R' is selected from the group consisting of hydrogen, (C$_1$-C$_6$)alkyl, —C(O)(C$_1$-C$_6$)alkyl, —C(O)O(C$_1$-C$_6$)alkyl and —S(O)$_2$(C$_1$-C$_6$)alkyl; and "------" represents a single bond; and ring B is

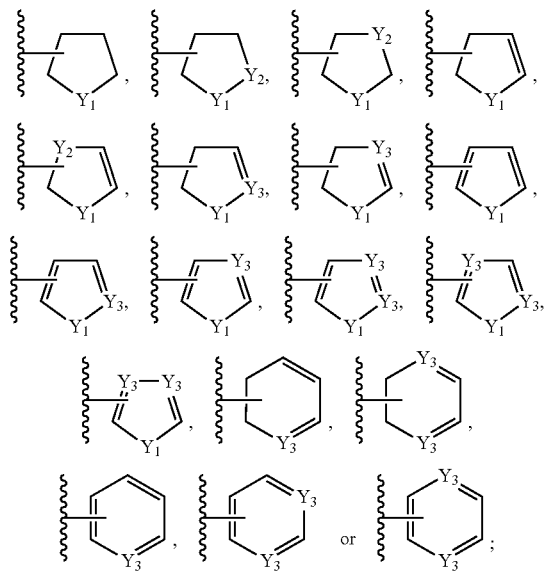

wherein Y$_1$ is —O—, —S— or —NR$_x$; Y$_2$ at each occurrence is independently selected from a group consisting of —O—, —S—, —NH—, —N(C$_1$-C$_6$)alkyl and —C(R$_y$)$_2$; Y$_3$ at each occurrence is independently selected from —N— or —CR$_y$; wherein R$_x$ is hydrogen, (C$_1$-C$_6$)alkyl, —C(O)(C$_1$-C$_6$)alkyl, —C(O)O(C$_1$-C$_6$)alkyl or —S(O)$_2$(C$_1$-C$_6$)alkyl; R$_y$ at each occurrence is independently selected from the group consisting of hydrogen, halogen, oxo, cyano, nitro, —NR$_5$R$_6$, —C(O)R$_5$, —C(O)NR$_5$R$_6$, —S(O)$_t$R$_7$, (C$_1$-C$_6$)alkyl, halo(C$_1$-C$_6$)alkyl, hydroxy, —O(C$_1$-C$_6$)alkyl, —(C$_3$-C$_8$)cycloalkyl, (C$_6$-C$_{10}$)aryl, —O(C$_1$-C$_6$)aryl, heterocyclyl and heteroaryl.

In another embodiment, the compound of Formula (I) encompasses a compound of Formula (Ia); wherein X$_1$ is —O— and X$_2$ is —CR'—; wherein R' is selected from the group consisting of hydrogen, (C$_1$-C$_6$)alkyl, —C(O)(C$_1$-C$_6$)alkyl, —C(O)O(C$_1$-C$_6$)alkyl and —S(O)$_2$(C$_1$-C$_6$)alkyl; and "------" represents a single bond; and ring B is

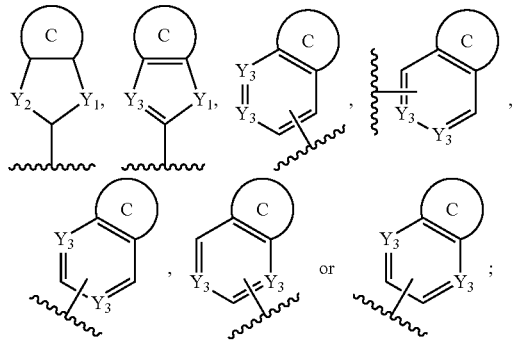

wherein ring C is selected from the group consisting of (C$_3$-C$_6$)cycloalkyl, (C$_6$-C$_{10}$)aryl, 5- or 6-membered heteroaryl and 5- or 6-membered heterocyclyl ring containing one or two heteroatoms independently selected from the group consisting of O, N and S; and Y$_1$, Y$_2$ and Y$_3$ are as defined above.

In another embodiment, the compound of Formula (I) encompasses a compound of Formula (Ia); wherein X$_1$ is —O— and X$_2$ is —CR'—; wherein R' is selected from the group consisting of hydrogen, (C$_1$-C$_6$)alkyl, —C(O)(C$_1$-C$_6$) alkyl, —C(O)O(C$_1$-C$_6$)alkyl and —S(O)$_2$(C$_1$-C$_6$)alkyl; and "------" represents a single bond; ring A is phenyl and ring B is

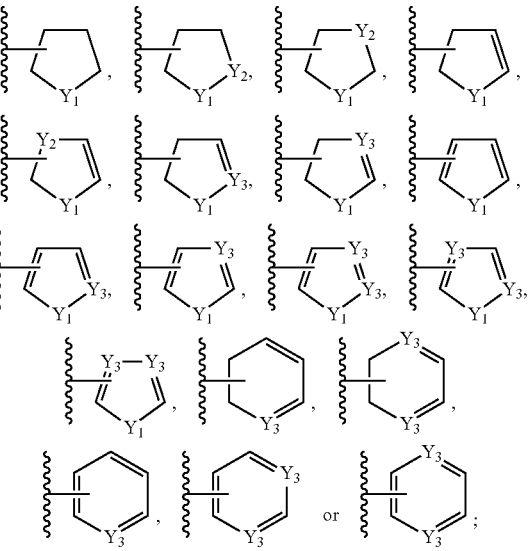

wherein Y$_1$ is —O—, —S— or —NR$_x$; Y$_2$ at each occurrence is independently selected from a group consisting of —O—, —S—, —NH—, —N(C$_1$-C$_6$)alkyl and —C(R$_y$)$_2$; Y$_3$ at each occurrence is independently selected from —N— or —CR$_y$; wherein R$_x$ is hydrogen, (C$_1$-C$_6$)alkyl, —C(O)(C$_1$-C$_6$)alkyl, —C(O)O(C$_1$-C$_6$)alkyl or —S(O)$_2$(C$_1$-C$_6$)alkyl; R$_y$ at each occurrence is independently selected from the group consisting of hydrogen, halogen, oxo, cyano, nitro, —NR$_5$R$_6$, —C(O)R$_5$, —C(O)NR$_5$R$_6$, —S(O)$_t$R$_7$, (C$_1$-C$_6$)alkyl, halo(C$_1$-C$_6$)alkyl, hydroxy, —O(C$_1$-C$_6$)alkyl, —(C$_3$-C$_8$)cycloalkyl, (C$_6$-C$_{10}$) aryl, —O(C$_1$-C$_6$)aryl, heterocyclyl and heteroaryl.

In another embodiment, the compound of Formula (I) encompasses a compound of Formula (Ia); wherein X$_1$ is —O— and X₂ is —CR'—; wherein R' is selected from the group consisting of hydrogen, (C₁-C₆)alkyl, —C(O)(C₁-C₆)alkyl, —C(O)O(C₁-C₆)alkyl and —S(O)₂(C₁-C₆)alkyl; and "------" represents a single bond; ring A is phenyl and ring B is

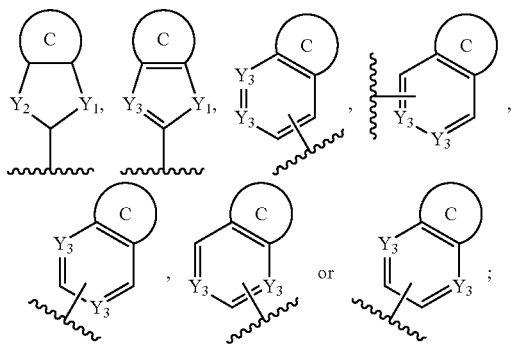

wherein ring C is selected from the group consisting of (C₃-C₆)cycloalkyl, (C₆-C₁₀)aryl, 5- or 6-membered heteroaryl and 5- or 6-membered heterocyclyl ring containing one or two heteroatoms independently selected from the group consisting of O, N and S; and Y₁, Y₂ and Y₃ are as defined above.

In an embodiment, the compound of Formula (I) encompasses a compound of Formula (Ia); wherein n is 2, 3 or 4.

In an embodiment, the compound of Formula (I) encompasses a compound of Formula (Ia); wherein n is 3.

In an embodiment, the compound of Formula (I) encompasses a compound of Formula (Ia); wherein R₃ is halogen.

In an embodiment, the compound of Formula (I) encompasses a compound of Formula (Ia); wherein R₃ is F, Cl or Br.

In an embodiment, the compound of Formula (I) encompasses a compound of Formula (Ia); wherein R₃ is F.

Representative compounds of the present invention include:
4-(2-(2-(5-Cyclopropylthiophen-2-yl)-5-fluorophenyl)benzofuran-5-yl)butanoic acid;
4-(2-(5-Fluoro-2-(5-(1-methylcyclopropyl)thiophen-2-yl)phenyl)benzofuran-5-yl)butanoic acid;
4-(2-(2-(5-Cyclopropylthiazol-2-yl)-5-fluorophenyl)benzofuran-5-yl)butanoic acid;
4-(2-(2-(5,6-Dihydro-4H-cyclopenta[d]thiazol-2-yl)-5-fluorophenyl)benzofuran-5-yl)butanoic acid;
4-(2-(5-Fluoro-2-(4,5,6,7-tetrahydrobenzo[d]thiazol-2-yl)phenyl)benzofuran-5-yl)butanoic acid;
4-(2-(5-Fluoro-2-(isoindolin-5-yl)phenyl)benzofuran-5-yl)butanoic acid;
4-(2-(2-(5,7-Dihydrofuro[3,4-b]pyridin-3-yl)-5-fluorophenyl)benzofuran-5-yl)butanoic acid; and
4-(2-(2-(6,7-Dihydro-5H-cyclopenta[b]pyridin-3-yl)-5-fluorophenyl)benzofuran-5-yl)butanoic acid
or an isotopic form, a stereoisomer, a tautomer, a pharmaceutically acceptable salt, a pharmaceutically acceptable solvate, a prodrug, a polymorph, N-oxide, S-oxide, or a carboxylic acid isostere thereof.

In another aspect of the present invention, there is provided a process for the preparation of the compounds of Formula (I) or pharmaceutically acceptable salts thereof.

The compounds of Formula (I) can be prepared by various methods including using methods well known to a person skilled in the art. Examples of processes for the preparation of a compound of Formula (I) are described below and illustrated in the following scheme but are not limited thereto. It will be appreciated by persons skilled in the art that within the process described herein, the order of the synthetic steps employed may be varied and will depend inter alia on factors such as the nature of functional groups present in a particular substrate and the protecting group strategy (if any) to be adopted. Clearly, such factors will also influence the choice of reagents such as bases, solvents or coupling agents to be used in the reaction steps.

The reagents, reactants and intermediates used in the following processes are either commercially available or can be prepared according to standard procedures known in the art, for instance those reported in the literature references.

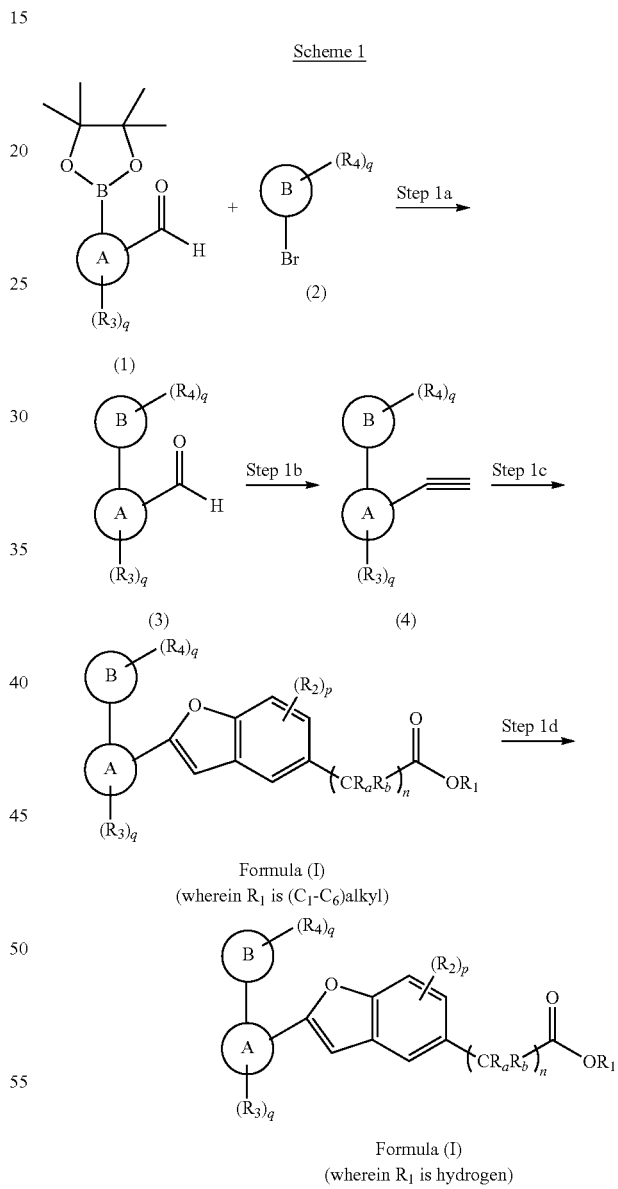

Scheme 1

In one embodiment, there is provided a processes for the preparation of the compound of Formula (I), wherein
X₁ is —O—;
X₂ is —CR'—;
Ring A is (C₆-C₁₀)aryl or 5- to 10-membered heteroaryl;
Ring B is (C₃-C₈)cycloalkyl, (C₅-C₈)cycloalkenyl, (C₆-C₁₀)aryl, 5- to 10-membered heteroaryl or a saturated or partially unsaturated 3- to 11-membered heterocyclyl ring containing one to four heteroatoms independently selected from the group consisting of O, N and S;

$R_1$ is hydrogen or $(C_1-C_6)$alkyl;

$R_2$ at each occurrence is independently selected from the group consisting of hydrogen, halogen, hydroxy, cyano, nitro, $-NR_5R_6$, $-C(O)R_5$, $-C(O)NR_5R_6$, $-S(O)_tR_7$, $(C_1-C_6)$alkyl, halo$(C_1-C_6)$alkyl, $-O(C_1-C_6)$alkyl and $(C_6-C_{10})$aryl;

$R_3$ and $R_4$ at each occurrence are independently selected from the group consisting of hydrogen, halogen, oxo, cyano, nitro, $-NR_5R_6$, $-C(O)R_5$, $-C(O)NR_5R_6$, $-S(O)_tR_7$, $(C_1-C_6)$alkyl, halo$(C_1-C_6)$alkyl, hydroxy, $-O(C_1-C_6)$alkyl, $(C_3-C_8)$cycloalkyl, $(C_6-C_{10})$aryl, $-O(C_1-C_6)$aryl, heterocyclyl and heteroaryl;

$R_5$ and $R_6$ are independently selected from the group consisting of hydrogen, $(C_1-C_6)$alkyl, $(C_6-C_{10})$aryl, heterocyclyl and heteroaryl;

$R_7$ is hydrogen, $(C_1-C_6)$alkyl or $-NR_5R_6$;

R' and R'' are independently selected from the group consisting of hydrogen, $(C_1-C_6)$alkyl, $-C(O)(C_1-C_6)$alkyl, $-C(O)O(C_1-C_6)$alkyl and $-S(O)_2(C_1-C_6)$alkyl; or R' and R'' are taken together to form oxo, $(C_3-C_8)$cycloalkyl, $(C_5-C_8)$cycloalkenyl, or 3- to 6-membered saturated or a partially unsaturated heterocyclyl ring containing one or two heteroatoms independently selected from the group consisting of O, N and S;

$R_a$ and $R_b$ at each occurrence are independently selected from the group consisting of hydrogen, halogen and $(C_1-C_6)$alkyl;

n is an integer from 1 to 6;
p is an integer from 1 to 3;
q is an integer from 1 to 4;
t is an integer from 0 to 2;
------- represents presence or absence of a single bond;
wherein, $(C_1-C_6)$alkyl is unsubstituted or substituted with one or more groups independently selected from the group consisting of halogen, hydroxy, cyano, nitro, $-NR_6R_6$, $-C(O)R_5$, $-C(O)NR_5R_6$, $-S(O)_tR_7$, $(C_1-C_6)$alkyl, halo$(C_1-C_6)$alkyl, $-O(C_1-C_6)$alkyl, $(C_3-C_8)$cycloalkyl, $(C_6-C_{10})$aryl, heterocyclyl and heteroaryl; wherein $R_5$, $R_6$, $R_7$ and t are as defined above;

$-O(C_1-C_6)$alkyl is unsubstituted or substituted with one or more groups independently selected from the group consisting of halogen, hydroxy, cyano, nitro, $-NR_5R_6$, $-C(O)R_5$, $-C(O)NR_5R_6$, $-S(O)_tR_7$, $(C_1-C_6)$alkyl, halo$(C_1-C_6)$alkyl, $(C_3-C_8)$cycloalkyl, $(C_6-C_{10})$aryl and heterocyclyl; wherein $R_5$, $R_6$, $R_7$ and t are as defined above;

$(C_3-C_8)$cycloalkyl is unsubstituted or substituted with one or more groups independently selected from the group consisting of oxo, halogen, hydroxy, cyano, nitro, $-NR_5R_6$, $-C(O)R_5$, $-C(O)NR_5R_6$, $-S(O)_tR_7$, $(C_1-C_6)$alkyl, halo$(C_1-C_6)$alkyl and $-O(C_1-C_6)$alkyl; wherein $R_5$, $R_6$, $R_7$ and t are as defined above;

$(C_5-C_8)$cycloalkenyl is unsubstituted or substituted with one or more groups independently selected from the group consisting of halogen, hydroxy, cyano, nitro, $-NR_5R_6$, $-C(O)R_5$, $-C(O)NR_5R_6$, $-S(O)_tR_7$, $(C_1-C_6)$alkyl, halo$(C_1-C_6)$alkyl and $-O(C_1-C_6)$alkyl; wherein $R_5$, $R_6$, $R_7$ and t are as defined above;

$(C_6-C_{10})$aryl is unsubstituted or substituted with one or more groups independently selected from the group consisting of halogen, hydroxy, cyano, nitro, $-C(O)R_5$, $-C(O)OR_5$, $-S(O)_tR_7$, $-NR_5R_6$, $(C_1-C_6)$alkyl, halo$(C_1-C_6)$alkyl, $-O(C_1-C_6)$alkyl, halo$(C_1-C_6)$alkoxy, $(C_3-C_8)$cycloalkyl, $(C_6-C_{10})$aryl, $-O(C_6-C_{10})$aryl, heterocyclyl and heteroaryl, wherein $R_5$, $R_6$, $R_7$ and t are as defined above;

heterocyclyl is a 3- to 11-membered ring, which is unsubstituted or substituted with one or more groups independently selected from the group consisting of halogen, hydroxy, cyano, nitro, $-C(O)R_5$, $-C(O)OR_5$, $-S(O)_tR_7$, $-NR_5R_6$, $(C_1-C_6)$alkyl, halo$(C_1-C_6)$alkyl, $-O(C_1-C_6)$alkyl, halo$(C_1-C_6)$alkoxy, $(C_3-C_8)$cycloalkyl, $(C_6-C_{10})$aryl, heterocyclyl and heteroaryl; wherein $R_5$, $R_6$, $R_7$ and t are as defined above;

heteroaryl is a 5- to 10-membered ring, which is unsubstituted or substituted with one or more groups independently selected from the group consisting of halogen, hydroxy, cyano, nitro, $-C(O)R_5$, $-C(O)OR_5$, $-S(O)_tR_7$, $-NR_5R_6$, $(C_1-C_6)$alkyl, halo$(C_1-C_6)$alkyl, $-O(C_1-C_6)$alkyl, halo$(C_1-C_6)$alkoxy, $(C_3-C_8)$cycloalkyl, $(C_6-C_{10})$aryl, heterocyclyl and heteroaryl; wherein $R_5$, $R_6$, $R_7$ and t are as defined above;

halogen is chlorine, bromine, iodine or fluorine;
wherein said process consists the reaction steps as depicted in the above Scheme 1. The reactions steps of the process are described below:

Step 1a:

This process step involves reacting dioxaborolan derivative (compound (1) wherein $R_3$, Ring A and q are as defined above) with compound (2) (wherein $R_4$, Ring B and q are as defined above) in a solvent such as dichloromethane, THF, toluene, acetonitrile, dioxane, water or a mixture thereof, in the presence of a base selected from potassium hydroxide (KOH), sodium hydroxide (NaOH), potassium carbonate ($K_2OC_3$) or sodium carbonate ($Na_2CO_3$) and a palladium catalyst, such as palladium tetrakistriphenylphosphine [Pd(PPh$_3$)$_4$] or [1,1'-bis(diphenylphosphino)ferrocene]dichloropalladium(II), at a temperature ranging from 100 to 120° C. for a time period ranging from 5 to 15 minutes, to obtain the compound (3), (wherein Ring A, Ring B, $R_3$, $R_4$ and q are as defined above).

Step 1b:

In this process step, the compound (3) is subjected to Seyferth-Gilbert homologation (Synthetic Communications 2008, 39 (2), 299-310). Compound (3) is treated with dimethyl (1-diazo-2-oxopropyl)phosphonate in the presence of a base such as dry potassium carbonate in a solvent selected from methanol, ethanol, isopropyl alcohol or mixture thereof to obtain the compound (4), (wherein Ring A, Ring B, $R_3$, $R_4$ and q are as defined above).

Step 1c:

In this process step, the compound (4) is subjected to Sonogashira coupling (Org. Process Res. Dev., 2010, 14 (1), 180-187). Compound (4) is treated with a compound of formula

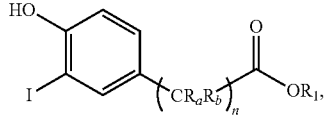

(wherein $R_1$ is $(C_1-C_6)$alkyl; $R_a$, $R_b$ and n are as defined above), in the presence of copper(I) iodide, a base such as triethylamine, palladium catalyst such as bis(triphenylphosphine)palladium(II) dichloride and a solvent selected from dioxane, DMF, toluene, THF or acetonitrile to obtain the compound of Formula (I) (wherein $R_1$ is $(C_1-C_6)$alkyl).

Step 1d:

The compound of Formula (I) (obtained in Step 1c), is taken in a solvent selected from THF, ethanol, MeOH, water or a mixture thereof, and hydrolyzed using a base selected from NaOH, KOH, Lithium hydroxide (LiOH) or barium hydroxide (Ba(OH)$_2$), to obtain the compound of Formula (I) (wherein R$_1$ is hydrogen).

The compounds of Formula (I) can be converted into their pharmaceutically acceptable salts by following procedure known to persons skilled in the art.

The pharmaceutically acceptable salts of the compounds of Formula (I) are prepared with relatively non-toxic acids or bases, depending on the particular substituents found on the compounds described herein. When the compounds of Formula (I) of the present invention contain an acidic group they can form an addition salt with a suitable base. For example, pharmaceutically acceptable base addition salts of the compounds of the present invention may include their alkali metal salts such as sodium, potassium, calcium, magnesium, ammonium or an organic base addition salt. Examples of pharmaceutically acceptable organic base addition salts of the compounds of the present invention include those derived from organic bases like lysine, arginine, guanidine, diethanolamine, metformin or other organic bases known to a person skilled in the art.

When the compounds of Formula (I) of the present invention contain one or more basic groups, they can form an addition salt with an inorganic or an organic acid. Examples of pharmaceutically acceptable acid addition salts include those derived from inorganic acids like boric acid, perchloric acid, hydrochloric acid, hydrobromic acid, hydrofluoric acid, hydriodic acid, nitric acid, carbonic acid, monohydrogencarbonic acid, phosphoric acid, monohydrogenphosphoric acid, dihydrogenphosphoric acid, sulfuric acid, monohydrogensulfuric acid, phosphorous acids or other inorganic acids known to the person skilled in the art. Furthermore, examples of pharmaceutically acceptable acid addition salts include the salts derived from organic acids such as acetic acid, propionic acid, isobutyric acid, oxalic acid, malic acid acid, tartaric acid, citric acid, ascorbic, maleic acid, malonic acid, benzoic acid, succinic acid, suberic acid, fumaric acid, mandelic acid, phthalic acid, benzenesulfonic acid, toluenesulfonic acid, methanesulfonic acid, glucuronic acid, galacturonic acid, naphthoic acid, camphoric acid or other organic acids known to the person skilled in the art. Certain specific compounds of the present invention contain both basic and acidic functionalities that allow the compounds to be converted into either base or acid addition salts.

The pharmaceutically acceptable salts of the present invention can be synthesized from the subject compound i.e. the compound of Formula (I) which contains a basic or acidic moiety by conventional chemical methods. Generally, the pharmaceutically acceptable salts are prepared by contacting the free base or acid (the compounds of formula (I)) with a desired salt-forming inorganic or organic acid or a base in a suitable solvent or dispersant or by anion exchange or cation exchange with other salts. Suitable solvents are, for example, ethyl acetate, ethers, alcohols, acetone, or mixtures of these solvents.

In an embodiment of the present invention, the compound of Formula (I) or the compound of Formula (Ia) is provided as a pharmaceutically acceptable salt.

Those skilled in the art will recognize that the compounds of Formula (I) of the present invention contain asymmetric or chiral centres, and therefore exist in different stereoisomeric forms, as racemic mixtures of enantiomers, mixtures of diastereomers or enantiomerically or optically pure compounds. The term "chiral" refers to molecules which have the property of non-superimposability of the mirror image cohort, while the term "achiral" refers to molecules which are superimposable on their mirror image partner. It is intended that all stereoisomeric forms of the compounds of the invention, including but not limited to, diastereomers and enantiomers, as well as mixtures thereof such as racemic mixtures, geometric isomers form part of the present invention.

When the compounds of Formula (I) of the present invention contain one chiral centre, the compounds exist in two enantiomeric forms and the present invention includes both enantiomers and mixtures of enantiomers, such as the specific 50:50 mixture referred to as a racemic mixtures. The enantiomers can be resolved by methods known to those skilled in the art, such as formation of diastereoisomeric salts which may be separated, for example, by crystallization (see, CRC Handbook of Optical Resolutions via Diastereomeric Salt Formation by David Kozma (CRC Press, 2001)); formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired enantiomer is converted into another chemical entity by one of the separation procedures described above, a further step is required to liberate the desired enantiomeric form. Alternatively, specific enantiomers may be synthesized by asymmetric synthesis using optically active reagents, substrates, catalysts or solvents, or by converting one enantiomer into the other by asymmetric transformation. Designation of a specific absolute configuration at a chiral carbon of the compounds of the invention is understood to mean that the designated enantiomeric form of the compounds is in enantiomeric excess (ee) or in other words is substantially free from the other enantiomer. For example, the "R" forms of the compounds are substantially free from the "S" forms of the compounds and are, thus, in enantiomeric excess of the "S" forms. Conversely, "S" forms of the compounds are substantially free of "R" forms of the compounds and are, thus, in enantiomeric excess of the "R" forms. Enantiomeric excess, as used herein, is the presence of a particular enantiomer at greater than 50%. In a particular embodiment when a specific absolute configuration is designated, the enantiomeric excess of depicted compounds is at least about 90%. When a compound of Formula (I) of the present invention has two or more chiral carbons it can have more than two optical isomers and can exist in diastereoisomeric forms. For example, when there are two chiral carbons, the compound can have up to 4 optical isomers and 2 pairs of enantiomers ((S,S)/(R,R) and (R,S)/(S,R)). The pairs of enantiomers (e.g., (S,S)/(R,R)) are mirror image stereoisomers of one another. The stereoisomers that are not mirror-images (e.g., (S,S) and (R,S)) are diastereomers. The diastereoisomeric pairs may be separated by methods known to those skilled in the art, for example chromatography or crystallization and the individual enantiomers within each pair may be separated as described above. The present invention includes each diastereoisomer of such compounds and mixtures thereof.

The isotopically labelled forms of compounds of Formula (I), can be prepared by conventional techniques known to those skilled in the art or by processes analogous to those described above or in the subsequent section on examples by using a corresponding isotopically labelled reagent in place of the non-labelled reagent.

In one embodiment, the compounds of Formula (I) exists as tautomers, and it is intended to encompass all the tautomeric forms of the compounds within the scope of the present invention.

Furthermore, the present invention includes all the solvates of the compounds of Formula (I), for example, hydrates and the solvates formed with other solvents of crystallisation, selected from alcohols such as methanol, ethanol, 1-propanol or 2-propanol, ethers such as diethyl ether, isopropyl ether or tetrahydrofuran, esters such as methyl acetate or ethyl acetate, ketone such as acetone or their mixtures thereof. Certain compounds of the present invention can exist in unsolvated forms as well as solvated forms, including hydrated forms.

It is also intended to encompass various polymorphs of the compounds of Formula (I) within the scope of the present invention. Various polymorphs of the compounds of the present invention can be prepared by standard crystallisation procedures known in the art. The crystallisation technique employed can utilize various solvents or their mixtures, temperature conditions and various modes of cooling, ranging from very fast to very slow cooling. The presence of polymorphs can be determined by IR (Infra-red) spectroscopy, solid probe NMR (Nuclear Magnetic Resonance) spectroscopy, differential scanning calorimetry, powder X-ray diffraction or such other standard techniques.

Furthermore, the present invention also includes prodrugs of the compounds of Formula (I). The prodrugs of the compounds of the present invention are derivatives of the aforesaid compounds of the invention which upon administration to a subject in need thereof undergoes chemical conversion by metabolic or chemical processes to release the parent drug in vivo from which the prodrug is derived. The preferred prodrugs are pharmaceutically acceptable ester derivatives e.g., alkyl esters, cycloalkyl esters, alkenyl esters, benzyl esters, mono- or di-substituted alkyl esters convertible by solvolysis under physiological conditions to the parent carboxylic acid, and those conventionally used in the art.

The present invention also relates to carboxylic acid isosteres of the compounds of Formula (I).

The present invention also relates to N-oxide derivatives of the compounds of Formula (I).

The present invention also relates to S-oxide derivatives of the compounds of Formula (I).

In one aspect of the present invention, i.e. the compounds of Formula (I) are GPR120 agonists.

In an embodiment of the present invention, the compounds of Formula (I) find use in the treatment or prophylaxis of a disease or a disorder mediated by GPR120.

In another aspect, the present invention relates to a method for the treatment or prophylaxis of a disease or a disorder mediated by GPR120, comprising administering to a subject in need thereof, a therapeutically effective amount of a compound of Formula (I) or a stereoisomer, a tautomer, a pharmaceutically acceptable salt or a pharmaceutically acceptable solvate thereof.

In an embodiment, the present invention relates to use of the compound of Formula (I) or a stereoisomer, a tautomer, a pharmaceutically acceptable salt or a pharmaceutically acceptable solvate thereof; for the treatment or prophylaxis of a disease or a disorder mediated by GPR120.

According to one embodiment, the present invention relates to use of the compounds of Formula (I) or a stereoisomer, a tautomer, a pharmaceutically acceptable salt or a pharmaceutically acceptable solvate thereof; in the manufacture of a medicament for the treatment or prophylaxis of a disease or a disorder mediated by GPR120.

In an embodiment of the invention, the disease or disorder mediated by GPR120 is selected from the group consisting of diabetes, obesity, hyperglycemia, glucose intolerance, insulin resistance, hyperinsulinemia, hypercholesterolemia, hypertension, hyperlipoproteinemia, hyperlipidemia, hypertriglylceridemia, dyslipidemia, metabolic syndrome, cardiovascular disease, atherosclerosis, kidney disease, polycystic ovary syndrome, ketoacidosis, thrombotic disorders, diabetic nephropathy, diabetic neuropathy, diabetic retinopathy, sexual dysfunction, fatty liver development, dermatopathy, dyspepsia, hypoglycemia, cancer, edema and a disorder related to glucose levels such as pancreatic beta cell regeneration.

In an embodiment of the invention, the disease or disorder mediated by GPR120 is selected from the group consisting of diabetes, obesity, insulin resistance, hyperglycemia, glucose intolerance, hypercholesterolemia, hypertriglylceridemia, dyslipidemia, hyperlipoproteinemia, hyperinsulinemia, atherosclerosis, diabetic nephropathy, diabetic neuropathy, diabetic retinopathy, metabolic syndrome, hypertension and pancreatic beta cell degeneration.

In an embodiment of the invention, the disease or disorder mediated by GPR120 is selected from the group consisting of diabetes, obesity, insulin resistance, hyperglycemia, glucose intolerance, metabolic syndrome and pancreatic beta cell degeneration.

In an embodiment, the disease or disorder mediated by GPR120 is Type 2 diabetes.

In an embodiment, the disease or disorder mediated by GPR120 is a metabolic disorder which refers to one or more diseases or disorders as identified above.

In an embodiment, the disease or disorder mediated by GPR120 is an inflammatory disorder.

Accordingly, the present invention relates to a method for the treatment or prophylaxis of a metabolic disorder, comprising administering to a subject in need thereof a therapeutically amount of a compound of Formula (I) or a stereoisomer, a tautomer, or a pharmaceutically acceptable salt or a pharmaceutically acceptable solvate thereof.

In an embodiment, the present invention provides use of the compound of Formula (I) or a stereoisomer, a tautomer or a pharmaceutically acceptable salt thereof for the treatment or prophylaxis of a metabolic disorder.

According to one embodiment, the present invention relates to use of the compounds of Formula (I) or pharmaceutically acceptable salts thereof in the manufacture of a medicament, for the treatment or prophylaxis of a metabolic disorder.

In one embodiment, the metabolic disorder is selected from the group consisting of diabetes, obesity, cardiovascular disease, hypertension, ketoacidosis, insulin resistance, glucose intolerance, hyperglycemia, hypertriglylceridemia, polycystic ovary syndrome, hypercholesterolemia, hyperlipoproteinemia, dyslipidemia, metabolic syndrome, hyperlipidemia, diabetic nephropathy, diabetic neuropathy, diabetic retinopathy, edema and related disorders associated with abnormal plasma lipoprotein, triglycerides and pancreatic beta cell degeneration.

In an embodiment, the metabolic disorder is selected from the group consisting of diabetes, obesity, insulin resistance, hyperglycemia, glucose intolerance, hypercholesterolemia, hypertriglylceridemia, dyslipidemia, hyperlipoproteinemia, hyperinsulinemia, atherosclerosis, diabetic nephropathy, diabetic neuropathy, diabetic retinopathy, metabolic syndrome, hypertension and pancreatic beta cell degeneration.

In an embodiment, the metabolic disorder is selected from the group consisting of diabetes, obesity, insulin resistance, glucose intolerance, dyslipidemia, hyperinsulinemia, metabolic syndrome and pancreatic beta cell degeneration.

In an embodiment, the metabolic disorder is Type 2 diabetes.

Pharmaceutical Compositions

Furthermore, the present invention relates to pharmaceutical compositions that contain a therapeutically effective amount of at least one compound of Formula (I) or its pharmaceutically acceptable salt in addition to a customary pharmaceutically acceptable carrier, and to a process for the production of a pharmaceutical composition, which includes bringing at least one compound of Formula (I), into a suitable administration form using a pharmaceutically suitable and physiologically tolerable excipient and, if appropriate, further suitable active compounds, additives or auxiliaries.

According to one embodiment, the present invention relates to a pharmaceutical composition comprising the compounds of Formula (I) or pharmaceutically acceptable salts thereof and one or more pharmaceutically acceptable excipients; for use as GPR120 agonists.

According to another embodiment, the present invention relates to a pharmaceutical composition comprising the compounds of Formula (I) or pharmaceutically acceptable salts thereof and one or more pharmaceutically acceptable excipients; for use in the treatment or prophylaxis of a disease or a disorder mediated by GPR120.

It is further intended to include within the scope of the present invention the use of the compounds of Formula (I) or its pharmaceutically acceptable salts thereof in combination with at least one therapeutically active agent.

According to one embodiment, the present invention provides a pharmaceutical composition, comprising a therapeutically effective amount of a compound of Formula (I) or a pharmaceutically acceptable salt thereof and at least one further therapeutically active agent, together with a pharmaceutically acceptable carrier.

In an embodiment, the present invention relates to use of the compound of Formula (I) or a stereoisomer, a tautomer, a pharmaceutically acceptable salt or a pharmaceutically acceptable solvate thereof; in combination with a further therapeutically active agent, in the treatment or prophylaxis of a disease or a disorder mediated by GPR120.

The therapeutically active agent that can be used in combination with one or more of the compounds of Formula (I) is selected from the compounds or active substances known to be used in the treatment of diabetes and other conditions or disorders such as obesity, insulin resistance, hyperglycemia, glucose intolerance, hypercholesterolemia, hypertriglylceridemia, dyslipidemia, hyperlipoproteinemia, hyperinsulinemia or atherosclerosis. According to the present invention, the therapeutically active agent, used in combination with the compounds of Formula (I) of the present invention, include, but are not limited to, insulin, sulfonylureas, biguanidines, meglitinides, oxadiazolidinediones, thiazolidinediones, glucosidase inhibitors, inhibitors of glycogen phosphorylase, glucagon antagonists, HMGCoA reductase inhibitor, GLP-1 (Glucogen-like peptide-1) agonists, potassium channel openers, inhibitors of dipeptidylpeptidase IV (DPP-IV), diglyceride acyltransferase (DGAT) inhibitor, insulin sensitizers, modulators of glucose uptake, modulators of glucose transport and modulators of glucose reabsorption, modulators of the sodium-dependent glucose transporter 1 or 2 (SGLT1, SGLT2), compounds which alter lipid metabolism such as antihyperlipidemic active ingredients and antilipidemic active ingredients, PPARgamma agonists and agents with combined PPARalpha and gamma activity and active ingredients which act on the ATP-dependent potassium channel of the beta cells.

In an embodiment, the compound of Formula (I) can be used in combination with a PPAR gamma agonist selected from the group consisting of rosiglitazone, pioglitazone and rivoglitazone.

In an embodiment, the compound of Formula (I) can be used in combination with a HMGCoA reductase inhibitor selected from the group consisting of simvastatin, fluvastatin, pravastatin, lovastatin, atorvastatin, cerivastatin and rosuvastatin.

In an embodiment, the compound of Formula (I) can be used in combination with a sulfonylurea selected from the group consisting of tolbutamide, glibenclamide, glipizide and glimepiride.

In another embodiment, the compound of the Formula (I) can be used in combination with a meglitinide selected from the group consisting of repaglinide, nateglinide and mitiglinide.

In another embodiment, the compound of the Formula (I) can be used in combination with GLP-1 agonist selected from the group consisting of exenatide, liraglutide, taspoglutide albiglutide and lixisenatide.

In another embodiment, the compound of the Formula (I) can be used in combination with DPP-IV inhibitor selected from the group consisting of alogliptin, gemigliptin, linagliptin, saxagliptin, sitagliptin and vildagliptin.

Accordingly, in an embodiment the further therapeutically active agent that can be used in combination with one or more compounds of Formula (I) encompassed in the present invention, can be selected from one or more of the agents including, but not limited to, insulin, rosiglitazone, pioglitazone, rivoglitazone, simvastatin, fluvastatin, pravastatin, lovastatin, atorvastatin, cerivastatin, rosuvastatin, tolbutamide, glibenclamide, glipizide, glimepiride, repaglinide, nateglinide, mitiglinide, exenatide, liraglutide, taspoglutide albiglutide, lixisenatide, alogliptin, gemigliptin, linagliptin, saxagliptin, sitagliptin, vildagliptin and the like.

The pharmaceutical compositions according to the present invention are prepared in a manner known and familiar to one skilled in the art. Pharmaceutically acceptable inert inorganic and/or organic carriers and/or additives can be used in addition to the compounds of Formula (I) and/or their pharmaceutically acceptable salts. For the production of pills, tablets, coated tablets and hard gelatin capsules it is possible to use, for example, lactose, corn starch or derivatives thereof, gum arabic, magnesia or glucose, etc. Carriers for soft gelatin capsules and suppositories are, for example, fats, waxes, natural or hardened oils, etc. Suitable carriers for the production of solutions, for example injection solutions, or of emulsions or syrups are, for example, water, physiological sodium chloride solution or alcohols, for example, ethanol, propanol or glycerol, sugar solutions, such as glucose solutions or mannitol solutions, or a mixture of the various solvents which have been mentioned.

Further, the pharmaceutical composition of the present invention also contains additives such as, for example, fillers, antioxidants, emulsifiers, preservatives, flavours, solubilisers or colourants. The pharmaceutical composition of the present invention can also contain two or more compounds of Formula (I) or a stereoisomer, a tautomer, pharmaceutically acceptable salt or a pharmaceutically acceptable solvate thereof. The pharmaceutical compositions can also contain one or more other therapeutically or prophylactically active agents.

The pharmaceutical composition can contain about 1 to 99%, for example, about 10 to 80%, by weight of the compound of Formula (I) or a stereoisomer, a tautomer, pharmaceutically acceptable salt or a pharmaceutically acceptable solvate thereof.

The amount of the active ingredient i.e. the compound of Formula (I) or a stereoisomer, a tautomer, pharmaceutically acceptable salt in the pharmaceutical compositions can, for example, vary from about 1 to 500 mg. In case of higher body weight of the subject in need of the treatment, the pharmaceutical composition may contain the compound of Formula (I) or a stereoisomer, a tautomer, pharmaceutically acceptable salt or a pharmaceutically acceptable solvate thereof; in an amount ranging from 5 mg to 1000 mg. The desirable dosage of the compounds of Formula (I) can be selected over a wide range. The daily dosage to be administered is selected to achieve the desired therapeutic effect in subjects being treated for metabolic disorders. A dosage of about 0.05 to 50 mg/kg/day of the compounds of Formula (I) or a stereoisomer, a tautomer, pharmaceutically acceptable salt or a pharmaceutically acceptable solvate thereof may be administered. In case of higher body weight of the mammal in need of the treatment, a dosage of about 0.1 to 100 mg/kg/day of the compound of Formula (I) or a stereoisomer, a tautomer, pharmaceutically acceptable salt or a pharmaceutically acceptable solvate thereof may be administered. If required, higher or lower daily dosages can also be administered. Actual dosage levels of the active ingredients in the pharmaceutical composition of this present invention can be varied so as to obtain an amount of the active ingredient, which is effective to achieve the desired therapeutic response for a particular subject (patient), composition, and mode of administration without being toxic to the subject. The selected dosage level can be readily determined by a skilled medical practitioner in the light of the relevant circumstances, including the condition (diseases or disorder) to be treated, the chosen route of administration depending on a number of factors, such as age, weight and physical health and response of the individual patient, pharmacokinetics, severity of the disease and the like, factors known in the medical art.

The pharmaceutical compositions according to the present invention can be administered orally, for example in the form of pills, tablets, coated tablets, capsules, granules or elixirs. Administration, however, can also be carried out rectally, for example in the form of suppositories, or parenterally, for example intravenously, intramuscularly or subcutaneously, in the form of injectable sterile solutions or suspensions, or topically, for example in the form of solutions or transdermal patches, or in other ways, for example in the form of aerosols or nasal sprays.

It is understood that modifications that do not substantially affect the activity of the various embodiments of this invention are included within scope of the invention disclosed herein. Accordingly, the following examples are intended to illustrate but not to limit scope of the present invention.

EXPERIMENTAL

Nomenclature of the compounds exemplified in the present invention is derived from Chemdraw Ultra version 9.0.1 CambridgeSoft Corporation, Cambridge.

Reagents were purchased from commercial suppliers such as Combi-Blocks Inc., CA; and CombiPhos Catalysts, Inc. and were used as such.

Unless otherwise stated all temperatures are in degree Celsius. Also, in the examples and elsewhere, abbreviations have the following meanings:

The abbreviations and terms that are used herein:

| LIST OF ABBREVIATIONS | |
|---|---|
| ATP | Adenosine triphosphate |
| $CDCl_3$ | Deuterated chloroform |
| ° C. | Degree celcius |
| DMF | N,N-dimethyl formamide |
| DMSO | Dimethyl sulfoxide |
| EtOAc | Ethyl acetate |
| g | gram |
| h | hour |
| $LiOH \cdot H_2O$ | Lithium hydroxidemonohydrate |
| mg | milligram |
| MeOH | methanol |
| mmol | Millimoles |
| mL | Millilitre |
| nM | Nanomolar |
| μM | Micromolar |
| $Pd(PPh_3)_2Cl_2$ | Bis(triphenylphosphine) palladium(II) dichloride |
| PET | Petroleum Ether |
| RT | Room temperature (20° C.-25° C.) |
| THF | Tetrahydrofuran |

Example 1

4-(2-(2-(5-Cyclopropylthiophen-2-yl)-5-fluorophenyl)benzofuran-5-yl)butanoic acid (Compound 1)

Step 1a

Synthesis of 2-(5-cyclopropylthiophen-2-yl)-5-fluorobenzaldehyde

Potassium carbonate (851 mg, 6.15 mmol) was added to a solution of 5-fluoro-2-(4,4,5,5-tetramethyl-1,3,2-dioxaborolan-2-yl)benzaldehyde (commercial source, 923 mg, 3.69 mmol) and 2-bromo-5-cyclopropylthiophene (commercial source, 500 mg, 2.462 mmol) in dioxane:water (4:1) (4 mL) and the mixture was degassed with argon for 2 to 3 minutes. To the resulting solution, palladium tetrakis triphenylphosphine (35.6 mg, 0.123 mmol) was added and the mixture was again degassed with argon for 2 to 3 minutes. The mixture was then heated at 110° C. for 10 minutes in microwave. After completion of reaction, the compound was extracted with EtOAc, dried over sodium sulfate, concentrated and purified by column chromatography (silica gel column/EtOAc and PET as eluent) to obtain the title compound (248 mg, 1.007 mmol) as colorless thick liquid. Yield: 40.9%; $^1H$ NMR (300 MHz, $CDCl_3$): δ 10.14 (s, 1H), 7.67 (dd, J=3, 9 Hz, 1H), 7.52 (dd, J=5.1, 8.4 Hz, 1H), 7.33 (d, J=83, 8.1 Hz, 1H), 6.82 (dd, J=3.3, 5.1 Hz, 2H), 2.17-2.08 (m, 1H), 1.10-1.03 (m, 2H), 0.82-0.77 (m, 2H); HPLC: 95.67%, MS: (m/z) 247 (M+1).

Step 1b

Synthesis of 2-cyclopropyl-5-(2-ethynyl-4-fluorophenyl)thiophene

Dimethyl(1-diazo-2-oxopropyl)phosphonate (4680 mg, 2.436 mmol) was added slowly to the reaction mixture of 2-(5-cyclopropylthiophen-2-yl)-5-fluorobenzaldehyde (compound of Step 1a, 500 mg, 2.030 mmol) and dry potassium carbonate (561 mg, 4.06 mmol) in methanol. After completion of the reaction, solvent was evaporated, extracted with EtOAc, dried over sodium sulfate and purified by column chromatography to obtain the title compound (430 mg, 1.768 mmol) as pale yellow liquid. Yield: 87%; $^1$H NMR (300 MHz, CDCl$_3$): δ 7.46-7.41 (m, 1H), 7.36 (d, J=3.6 Hz, 1H), 7.29-7.26 (m, 1H), 7.10-7.03 (m, 1H), 6.76 (d, J=3.6 Hz, 1H), 3.29 (s, 1H), 2.15-2.07 (m, 1H), 1.07-1.00 (m, 2H), 0.82-0.77 (m, 2H); HPLC: 99.63%; MS: (m/z) 243.0 (M+H).

Step 1c

Synthesis of methyl 4-(2-(2-(5-cyclopropylthiophen-2-yl)-5-fluorophenyl)benzofuran-5-yl)butanoate To a solution of methyl 4-(4-hydroxy-3-iodophenyl)butanoate (0.1 g, 0.312 mmol) and copper(I) iodide (2.97 mg, 0.016 mmol) in DMF (1.5 mL) was added Pd(PPh$_3$)$_2$Cl$_2$ (8.77 mg, 0.012 mmol), copper(I) iodide (2.97 mg, 0.016 mmol) and triethylamine (0.087 mL, 0.625 mmol) under nitrogen atmosphere. The reaction mixture was stirred for 10 minutes, followed by addition of 2-cyclopropyl-5-(2-ethynyl-4-fluorophenyl)thiophene (compound of step 1 b, 0.151 g, 0.625 mmol) to the reaction mixture at RT. The reaction mixture was then heated to 60° C. for 2 hours and then stirred overnight at RT. After completion of reaction, the reaction mixture was filtered through celite Bed®. The residue was concentrated and purified by column chromatography to obtain the title compound as pale yellow semisolid.

$^1$H NMR (300 MHz, CDCl$_3$) δ: 7.70-7.69 (m, 1H), 7.41-7.37 (m, 2H), 7.13-7.02 (m, 2H), 6.76 (d, J=3.3 Hz, 1H), 6.74 (d, J=3.6 Hz, 1H), 6.22 (m, 1H), 3.68 (s, 3H), 2.72 (t, J=7.2 Hz, 2H), 2.35 (t, J=7.5 Hz, 2H), 2.15-2.08 (m, 1H), 2.01-1.94 (m, 2H), 1.07 (m, 2H), 0.81-0.77 (m, 2H); HPLC: 99.76%; MS: (m/z) 435.1 (M+H), 457.1 (M+Na).

Step 1d

Synthesis of 4-(2-(2-(5-cyclopropylthiophen-2-yl)-5-fluorophenyl)benzofuran-5-yl)butanoic acid To a solution of methyl 4-(2-(2-(5-cyclopropylthiophen-2-yl)-5-fluorophenyl)benzofuran-5-yl)butanoate (compound of step 1c, 40 mg, 0.092 mmol) in THF:MeOH (4:1) (4 mL) was added lithium hydroxide hydrate (19.31 mg, 0.460 mmol) then the mixture was allowed to stir at RT for 2 to 3 hours. After completion of the reaction, the solvent was removed. The reaction mixture was neutralized with saturated ammonium chloride, extracted with EtOAc, dried over sodium sulfate and concentrated to obtain the title compound as off-white solid. $^1$H NMR (300 MHz, DMSO-d$_6$): δ 12.04 (bs, 1H), 7.65-7.61 (m, 1H), 7.55-7.50 (m, 1H), 7.44 (d, J=8.7 Hz, 1H), 7.40 (s, 1H), 7.36-7.30 (m, 1H), 7.15 (d, J=7.2 Hz, 1H), 6.82 (d, J=3.6 Hz, 1H), 6.78 (d, J=3.3 Hz, 1H), 6.51 (s, 1H), 2.68 (t, J=7.2 Hz, 2H), 2.21 (t, J=7.5 Hz, 2H), 2.15-2.07 (m, 1H), 14.87-1.77 (m, 2H), 1.01-0.95 (m, 2H), 0.68-0.63 (m, 2H); HPLC: 98.84%; MS: (m/z) 421.1 (M+H).

Example 2

4-(2-(5-Fluoro-2-(5-(1-methylcyclopropyl)thiophen-2-yl)phenyl)benzofuran-5-yl)butanoic acid (Compound 2)

Step 2a

Synthesis of 5-fluoro-2-(5-(1-methylcyclopropyl)thiophen-2-yl)benzaldehyde

The title compound was prepared in an analogous manner as the compound of Step 1a of Example 1, by using 2-bromo-5-(1-methylcyclopropyl)thiophene instead of 2-bromo-5-cyclopropylthiophene. $^1$H NMR (300 MHz, CDCl$_3$) δ: 10.16 (s, 1H), 7.68-7.64 (m, 1H), 7.54-7.46 (m, 2H), 7.39-7.31 (m, 1H), 6.83-6.80 (m, 1H), 2.17-2.08 (m, 1H), 1.53 (s, 3H), 1.03-1.00 (m, 2H), 0.99-0.91 (m, 2H); HPLC: 80.84%, MS: (m/z) 261.0 (M+1).

Step 2b

Synthesis of 2-(2-ethynyl-4-fluorophenyl)-5-(1-methylcyclopropyl)thiophene

The title compound was prepared in an analogous manner as the compound of Step 1b of Example 1, by using 5-fluoro-2-(5-(1-methylcyclopropyl)thiophen-2-yl)benzaldehyde (compound of step 2a) instead of 2-(5-cyclopropylthiophen-2-yl)-5-fluorobenzaldehyde.

$^1$H NMR (300 MHz, CDCl$_3$): δ 7.47-7.42 (m, 1H), 7.38 (d, J=3.6 Hz, 1H), 7.31-7.26 (m, 1H), 7.11-7.03 (m, 1H), 6.76 (d, J=3.6 Hz, 1H), 3.29 (s, 1H), 1.52 (m, 3H), 1.02-0.94 (m, 2H), 0.90-0.82 (m, 2H); HPLC: 90.34%; MS: (m/z) 257.1 (M+H).

Step 2c

Synthesis of methyl 4-(2-(5-fluoro-2-(5-(1-methylcyclopropyl)thiophen-2-yl)phenyl)benzofuran-5-yl)butanoate The title compound was prepared in an analogous manner as the compound of Step 1c of Example 1, by using 2-(2-ethynyl-4-fluorophenyl)-5-(1-methylcyclopropyl)thiophene (compound of step 2b) instead of 2-cyclopropyl-5-(2-ethynyl-4-fluorophenyl)thiophene. $^1$H NMR (500 MHz, CDCl$_3$): δ 7.70-7.66 (m, 1H), 7.42-7.34 (m, 3H), 7.17-7.02 (m, 2H), 6.75-6.72 (m, 2H), 6.21 (s, 1H), 3.68 (s, 3H), 2.72 (t, J=7.5 Hz, 2H), 2.33 (t, J=7.5 Hz, 2H), 2.04-2.30 (m, 2H), 1.53 (s, 3H), 0.98-0.95 (m, 2H), 0.93-0.89 (m, 2H); HPLC: 98.47%; MS: (m/z) 449.1 (M+H).

Step 2d

Synthesis of 4-(2-(5-fluoro-2-(5-(1-methylcyclopropyl)thiophen-2-yl)phenyl)benzofuran-5-yl)butanoic acid The title compound was prepared in an analogous manner as the compound of Step 1d of Example 1, by using methyl 4-(2-(5-fluoro-2-(5-(1-methylcyclopropyl)thiophen-2-yl)phenyl)benzofuran-5-yl)butanoate (Compound of step 2c) instead of methyl 4-(2-(2-(5-cyclopropylthiophen-2-yl)-5-fluorophenyl)benzofuran-5-yl)butanoate.

¹HNMR (300 MHz, CDCl₃): δ 7.70-7.66 (m, 1H), 7.42-7.35 (m, 2H), 7.17-7.02 (m, 3H), 6.74-6.73 (m, 2H), 6.22 (s, 1H), 2.75 (t, J=7.2 Hz, 2H), 2.39 (t, J=7.5 Hz, 2H), 2.05-1.98 (m, 2H), 1.52 (s, 3H), 0.98-0.95 (m, 2H), 0.92-0.89 (m, 2H); HPLC: 93.82%; M:S (m/z) 435.1 (M+H).

Pharmacological Assays

Representative compounds of Formula (I) of the present invention (referred to as test compounds) were tested for their activity using the assays and the methods described below:

Beta (β) arrestin 2 Interaction Assay (BRET assay) was performed using CHO-K1 cells stably expressing the GPR120L receptor using β-galactosidase (Beta gal) enzyme fragment complementation assay. The measurement of GPR120 activation upon agonist activation was directly provided by β-arrestin recruitment. One day before the β-arrestin 2 assay, CHO-K1 cells were seeded and incubated overnight at 37° C. in a 5% CO₂ humidified atmosphere. Cells were treated with the test compounds in the various concentrations ranging from 30 µM to 1 nM and incubated for 2 hours for GPCR (GPR120) activation. Extent of Arrestin recruitment was measured by adding detection reagents for Beta gal complementation assay and was further incubated for 1 hour. The chemi-luminescent signal was detected on Polar Star (BMG Labtech). The dose-response curve was analyzed using Sigma Plot/Graph Pad. The $EC_{50}$ (concentration of the test compounds where 50% of compounds' maximal activity is observed) values were calculated from the dose-response curve.

The $EC_{50}$ values for the test compounds varied between 10 nM and 10 µM.

CONCLUSION

The $EC_{50}$ values determined for the test compounds by BRET assay is indicative of GPR120 agonist activity of the compounds of the present invention.

We claim:
1. A compound of formula (I);

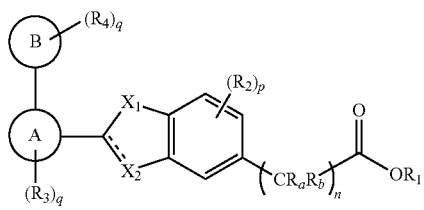

Formula (I)

wherein,
$X_1$ is —O—;
$X_2$ is —CR'—;
Ring A is $(C_6-C_{10})$aryl;
Ring B is $(C_6-C_{10})$aryl, 5- to 10-membered heteroaryl or a saturated or partially unsaturated 3- to 11-membered heterocyclyl ring containing one to four heteroatoms independently selected from the group consisting of O, N and S;
$R_1$ is hydrogen or $(C_1-C_6)$alkyl;
$R_2$ at each occurrence is independently selected from the group consisting of hydrogen, halogen, hydroxy, cyano, nitro, —$NR_5R_6$, —$C(O)R_5$, —$C(O)NR_5R_6$, —$S(O)_tR_7$, $(C_1-C_6)$alkyl, halo$(C_1-C_6)$alkyl, —$O(C_1-C_6)$alkyl and $(C_6-C_{10})$aryl;
$R_3$ and $R_4$ at each occurrence are independently selected from the group consisting of hydrogen, halogen, oxo, cyano, nitro, —$NR_5R_6$, —$C(O)R_5$, —$C(O)NR_5R_6$, —$S(O)_tR_7$, $(C_1-C_6)$alkyl, halo$(C_1-C_6)$alkyl, hydroxy, —$O(C_1-C_6)$alkyl, $(C_3-C_8)$cycloalkyl, $(C_6-C_{10})$aryl, —$O(C_6-C_{10})$aryl, heterocyclyl and heteroaryl;
$R_5$ and $R_6$ are independently selected from the group consisting of hydrogen, $(C_1-C_6)$alkyl, $(C_6-C_{10})$aryl, heterocyclyl and heteroaryl;
$R_7$ is hydrogen, $(C_1-C_6)$alkyl or —$NR_5R_6$;
R' is selected from the group consisting of hydrogen, $(C_1-C_6)$alkyl, —$C(O)(C_1-C_6)$alkyl, —$C(O)O(C_1-C_6)$alkyl and —$S(O)_2(C_1-C_6)$alkyl;
$R_a$ and $R_b$ at each occurrence are independently selected from the group consisting of hydrogen, halogen and $(C_1-C_6)$alkyl;
n is 3;
p is an integer from 1 to 3;
q is an integer from 1 to 4;
t is an integer from 0 to 2;
------- represents a single bond;
wherein,
$(C_1-C_6)$alkyl is unsubstituted or substituted with one or more groups independently selected from the group consisting of halogen, hydroxy, cyano, nitro, —$NR_5R_6$, —$C(O)R_5$, —$C(O)NR_5R_6$, —$S(O)_tR_7$, $(C_1-C_6)$alkyl, halo$(C_1-C_6)$alkyl, —$O(C_1-C_6)$alkyl, $(C_3-C_8)$cycloalkyl, $(C_6-C_{10})$aryl, heterocyclyl and heteroaryl; wherein $R_5$, $R_6$, $R_7$ and t are as defined above;
—$O(C_1-C_6)$alkyl is unsubstituted or substituted with one or more groups independently selected from the group consisting of halogen, hydroxy, cyano, nitro, —$NR_5R_6$, —$C(O)R_5$, —$C(O)NR_5R_6$, —$S(O)_tR_7$, $(C_1-C_6)$alkyl, halo$(C_1-C_6)$alkyl, $(C_3-C_8)$cycloalkyl, $(C_6-C_{10})$aryl and heterocyclyl; wherein $R_5$, $R_6$, $R_7$ and t are as defined above;
$(C_3-C_8)$cycloalkyl is unsubstituted or substituted with one or more groups independently selected from the group consisting of oxo, halogen, hydroxy, cyano, nitro, —$NR_5R_6$, —$C(O)R_5$, —$C(O)NR_5R_6$, —$S(O)_tR_7$, $(C_1-C_6)$alkyl, halo$(C_1-C_6)$alkyl and —$O(C_1-C_6)$alkyl; wherein $R_5$, $R_6$, $R_7$ and t are as defined above;
$(C_5-C_8)$cycloalkenyl is unsubstituted or substituted with one or more groups independently selected from the group consisting of halogen, hydroxy, cyano, nitro, —$NR_5R_6$, —$C(O)R_5$, —$C(O)NR_5R_6$, —$S(O)_tR_7$, $(C_1-C_6)$alkyl, halo$(C_1-C_6)$alkyl and —$O(C_1-C_6)$alkyl; wherein $R_5$, $R_6$, $R_7$ and t are as defined above;
$(C_6-C_{10})$aryl is unsubstituted or substituted with one or more groups independently selected from the group consisting of halogen, hydroxy, cyano, nitro, —$C(O)R_5$, —$C(O)OR_5$, —$S(O)_tR_7$, —$NR_5R_6$, $(C_1-C_6)$alkyl, halo$(C_1-C_6)$alkyl, —$O(C_1-C_6)$alkyl, halo$(C_1-C_6)$alkoxy, $(C_3-C_8)$cycloalkyl, $(C_6-C_{10})$aryl, —$O(C_6-C_{10})$aryl, heterocyclyl and heteroaryl, wherein $R_5$, $R_6$, $R_7$ and t are as defined above;
heterocyclyl is a 3- to 11-membered ring, which is unsubstituted or substituted with one or more groups independently selected from the group consisting of halogen, hydroxy, cyano, nitro, —$C(O)R_5$, —$C(O)OR_5$, —$S(O)_tR_7$, —$NR_5R_6$, $(C_1-C_6)$alkyl, halo$(C_1-C_6)$alkyl, —$O(C_1-C_6)$alkyl, halo$(C_1-C_6)$alkoxy, $(C_3-C_8)$cycloalkyl, $(C_6-C_{10})$aryl, heterocyclyl and heteroaryl; wherein $R_5$, $R_6$, $R_7$ and t are as defined above;
heteroaryl is a 5- to 10-membered ring, which is unsubstituted or substituted with one or more groups independently selected from the group consisting of halogen, hydroxy, cyano, nitro, —$C(O)R_5$, —$C(O)OR_5$, —$S(O)_tR_7$, —$NR_5R_6$, $(C_1-C_6)$alkyl, halo$(C_1-C_6)$alkyl, —$O(C_1-C_6)$alkyl, halo$(C_1-C_6)$alkoxy, $(C_3-C_8)$cycloalkyl, $(C_6-C_{10})$aryl, heterocyclyl and heteroaryl; wherein $R_5$, $R_6$, $R_7$ and t are as defined above;
halogen is chlorine, bromine, iodine or fluorine;

or an isotopic form, a stereoisomer, a tautomer, a pharmaceutically acceptable salt, a pharmaceutically acceptable solvate, a prodrug, a polymorph, N-oxide, S-oxide, or a carboxylic acid isostere thereof, wherein the carboxylic acid isostere is selected from:

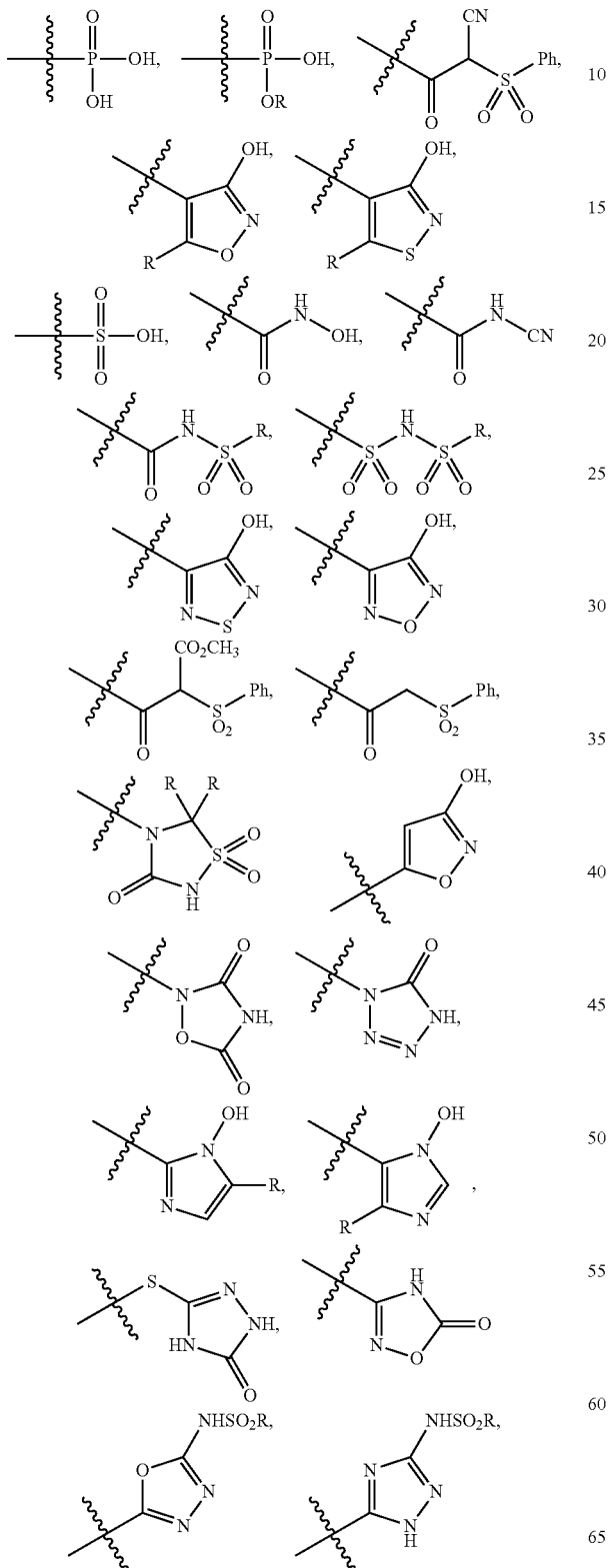

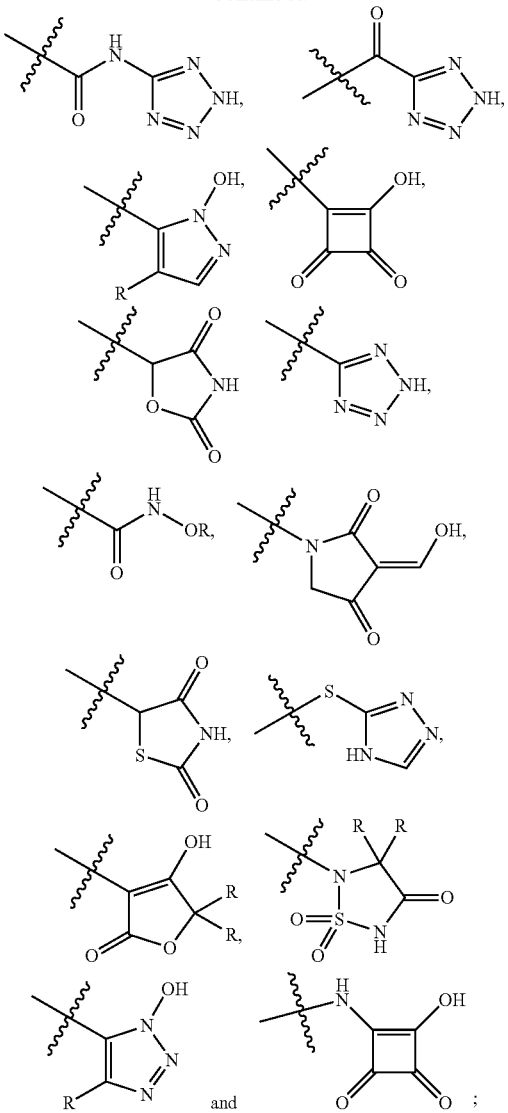

wherein R is hydrogen or $(C_1-C_3)$alkyl.

2. The compound according to claim 1, represented by Formula Ia

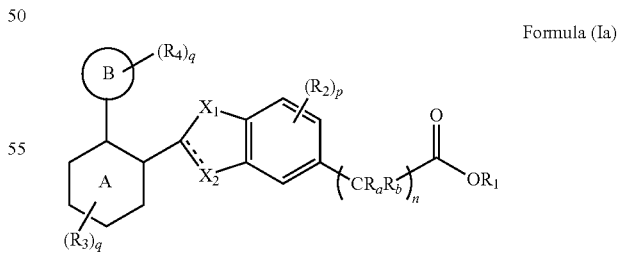

wherein,
$X_1$ is —O—;
$X_2$ is —CR'—
Ring A is phenyl;
Ring B is $(C_6-C_{10})$aryl, 5- to 10-membered heteroaryl or a saturated or partially unsaturated 3- to 11-membered heterocyclyl ring containing one to four heteroatoms independently selected from the group consisting of O, N and S;

$R_1$ is hydrogen or $(C_1-C_6)$alkyl;

$R_2$ at each occurrence is independently selected from the group consisting of hydrogen, halogen, hydroxy, cyano, nitro, $-NR_5R_6$, $-C(O)R_5$, $-C(O)NR_5R_6$, $-S(O)_tR_7$, $(C_1-C_6)$alkyl, halo$(C_1-C_6)$alkyl, $-O(C_1-C_6)$alkyl and $(C_6-C_{10})$aryl;

$R_3$ at each occurrence is independently selected from the group consisting of hydrogen, halogen, oxo, cyano, nitro, $-NR_5R_6$, $-C(O)R_5$, $-C(O)NR_5R_6$, $-S(O)_tR_7$, $(C_1-C_6)$alkyl, halo$(C_1-C_6)$alkyl, hydroxy and $-O(C_1-C_6)$alkyl;

$R_4$ at each occurrence is independently selected from the group consisting of hydrogen, halogen, oxo, cyano, nitro, $-NR_5R_6$, $-C(O)R_5$, $-C(O)NR_5R_6$, $-S(O)_tR_7$, $(C_1-C_6)$alkyl, halo$(C_1-C_6)$alkyl, hydroxy, $-O(C_1-C_6)$alkyl, $(C_3-C_8)$cycloalkyl, $(C_6-C_{10})$aryl, $-O(C_1-C_6)$aryl, heterocyclyl and heteroaryl;

$R_5$ and $R_6$ at each occurrence are independently selected from the group consisting of hydrogen, $(C_1-C_6)$alkyl, $(C_6-C_{10})$aryl, heterocyclyl and heteroaryl;

$R_7$ is hydrogen, $(C_1-C_6)$alkyl or $-NR_5R_6$;

R' is selected from the group consisting of hydrogen, $(C_1-C_6)$alkyl, $-C(O)(C_1-C_6)$alkyl, $-C(O)O(C_1-C_6)$alkyl and $-S(O)_2(C_1-C_6)$alkyl;

$R_a$ and $R_b$ at each occurrence are independently selected from the group consisting of hydrogen, halogen and $(C_1-C_6)$alkyl;

n is 3;

p is an integer from 1 to 3;

q is an integer from 1 to 4;

t is an integer from 0 to 2;

------- represents a single bond;

wherein, $(C_1-C_6)$alkyl is unsubstituted or substituted with one or more groups independently selected from the group consisting of halogen, hydroxy, cyano, nitro, $-NR_5R_6$, $-C(O)R_5$, $-C(O)NR_5R_6$, $-S(O)_tR_7$, $(C_1-C_6)$alkyl, halo$(C_1-C_6)$alkyl, $-O(C_1-C_6)$alkyl, $(C_3-C_8)$cycloalkyl, $(C_6-C_{10})$aryl, heterocyclyl and heteroaryl; wherein $R_5$, $R_6$, $R_7$ and t are as defined above;

$-O(C_1-C_6)$alkyl is unsubstituted or substituted with one or more groups independently selected from the group consisting of halogen, hydroxy, cyano, nitro, $-NR_5R_6$, $-C(O)R_5$, $-C(O)NR_5R_6$, $-S(O)_tR_7$, $(C_1-C_6)$alkyl, halo$(C_1-C_6)$alkyl, $(C_6-C_{10})$aryl, $(C_3-C_8)$cycloalkyl, and heterocyclyl; wherein $R_5$, $R_6$, $R_7$ and t are as defined above;

$(C_3-C_8)$cycloalkyl is unsubstituted or substituted with one or more groups independently selected from the group consisting of oxo, halogen, hydroxy, cyano, nitro, $-NR_5R_6$, $-C(O)R_5$, $-C(O)NR_5R_6$, $-S(O)_tR_7$, $(C_1-C_6)$alkyl, halo$(C_1-C_6)$alkyl and $-O(C_1-C_6)$alkyl; wherein $R_5$, $R_6$, $R_7$ and t are as defined above;

$(C_5-C_8)$cycloalkenyl is unsubstituted or substituted with one or more groups independently selected from the group consisting of halogen, hydroxy, cyano, nitro, $-NR_5R_6$, $-C(O)R_5$, $-C(O)NR_5R_6$, $-S(O)_tR_7$, $(C_1-C_6)$alkyl, halo$(C_1-C_6)$alkyl and $-O(C_1-C_6)$alkyl; wherein $R_5$, $R_6$, $R_7$ and t are as defined above;

$(C_6-C_{10})$aryl is unsubstituted or substituted with one or more groups independently selected from the group consisting of halogen, hydroxy, cyano, nitro, $-C(O)R_5$, $-C(O)OR_5$, $-S(O)_tR_7$, $-NR_5R_6$, $(C_1-C_6)$alkyl, halo$(C_1-C_6)$alkyl, $-O(C_1-C_6)$alkyl, halo$(C_1-C_6)$alkoxy, $(C_3-C_8)$cycloalkyl, $(C_6-C_{10})$aryl, $-O(C_6-C_{10})$aryl, heterocyclyl and heteroaryl, wherein $R_5$, $R_6$, $R_7$ and t are as defined above;

heterocyclyl is a 3- to 11-membered ring, which is unsubstituted or substituted with one or more groups independently selected from the group consisting of halogen, hydroxy, cyano, nitro, $-C(O)R_5$, $-C(O)OR_5$, $-S(O)_tR_7$, $-NR_5R_6$, $(C_1-C_6)$alkyl, halo$(C_1-C_6)$alkyl, $-O(C_1-C_6)$alkyl, halo$(C_1-C_6)$alkoxy, $(C_3-C_8)$cycloalkyl, $(C_6-C_{10})$aryl, heterocyclyl and heteroaryl; wherein $R_5$, $R_6$, $R_7$ and t are as defined above;

heteroaryl is a 5- to 10-membered ring, which is unsubstituted or substituted with one or more groups independently selected from the group consisting of halogen, hydroxy, cyano, nitro, $-C(O)R_5$, $-C(O)OR_5$, $-S(O)_tR_7$, $-NR_5R_6$, $(C_1-C_6)$alkyl, halo$(C_1-C_6)$alkyl, $-O(C_1-C_6)$alkyl, halo$(C_1-C_6)$alkoxy, $(C_3-C_8)$cycloalkyl, $(C_6-C_{10})$aryl, heterocyclyl and heteroaryl; wherein $R_5$, $R_6$, $R_7$ and t are as defined above;

halogen is chlorine, bromine, iodine or fluorine;

or an isotopic form, a stereoisomer, a tautomer, a pharmaceutically acceptable salt, a pharmaceutically acceptable solvate, a prodrug, a polymorph, N-oxide, S-oxide, or a carboxylic acid isostere thereof, wherein the carboxylic acid isostere is selected from:

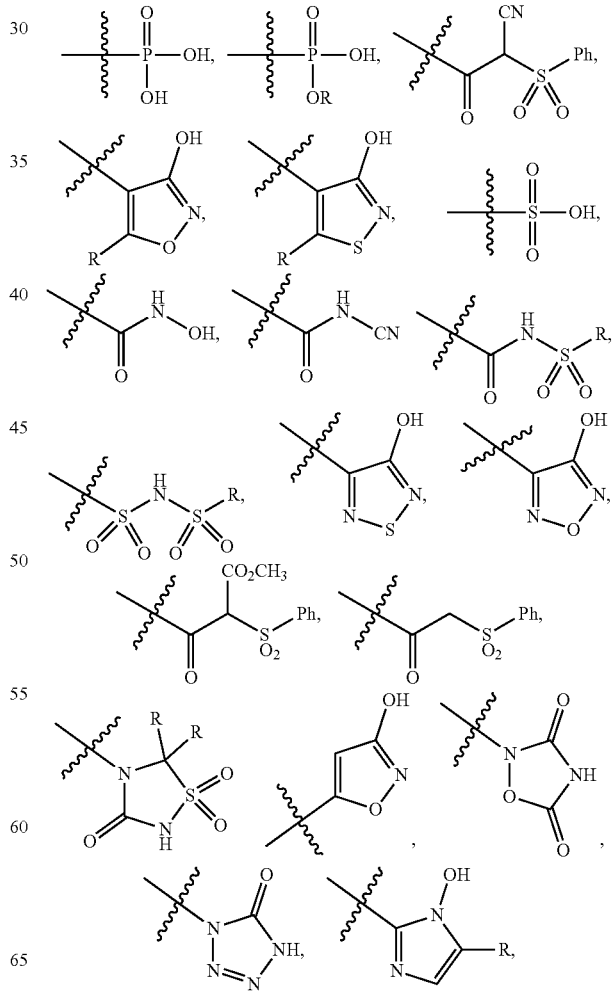

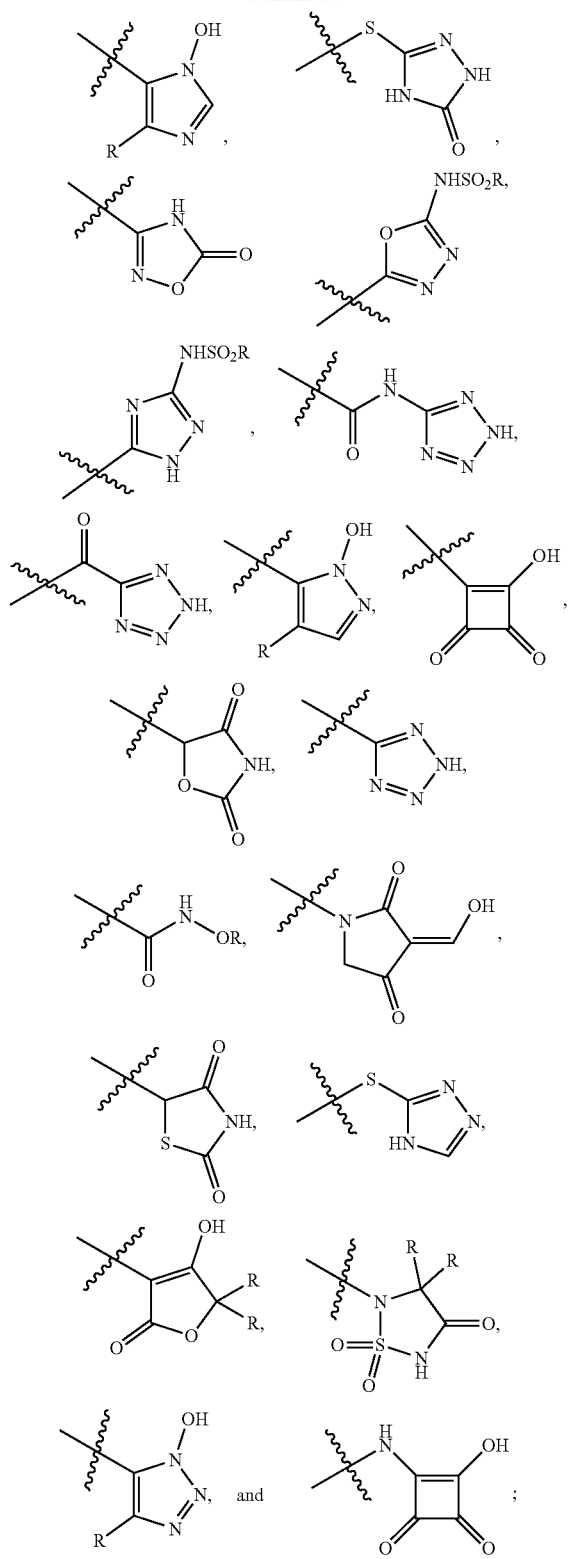

wherein R is hydrogen or $(C_1-C_3)$alkyl.

3. The compound according to claim 2, wherein ring A is phenyl; wherein R' is selected from the group consisting of hydrogen, $(C_1-C_6)$alkyl, —C(O)$(C_1-C_6)$alkyl, —C(O)O$(C_1-C_6)$alkyl and —S(O)$_2$$(C_1-C_6)$alkyl.

4. The compound according to claim 2, wherein ring B is

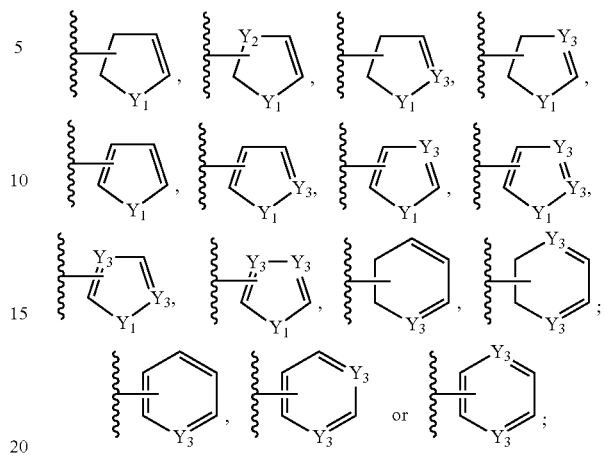

wherein $Y_1$ is —O—, —S— or —NR$_x$; $Y_2$ at each occurrence is independently selected from a group consisting of —O—, —S—, —NH—, —N$(C_1-C_6)$ alkyl and —C$(R_y)_2$; $Y_3$ at each occurrence is independently selected from —N— or —CR$_y$; wherein R$_x$ is hydrogen, $(C_1-C_6)$alkyl, —C(O)$(C_1-C_6)$alkyl, —C(O)O$(C_1-C_6)$alkyl or —S(O)$_2$$(C_1-C_6)$alkyl; R$_y$ at each occurrence is independently selected from the group consisting of hydrogen, halogen, oxo, cyano, nitro, —NR$_5$R$_6$, —C(O)R$_5$, —C(O)NR$_5$R$_6$, —S(O)$_t$R$_7$, $(C_1-C_6)$alkyl, halo$(C_1-C_6)$alkyl, hydroxy, —O$(C_1-C_6)$alkyl, —$(C_3-C_8)$cycloalkyl, $(C_6-C_{10})$aryl, —O$(C_1-C_6)$aryl, heterocyclyl and heteroaryl.

5. The compound according to claim 2, wherein ring B is

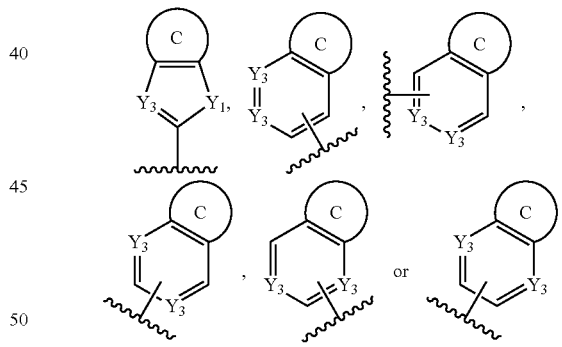

wherein ring C is selected from the group consisting of $(C_3-C_6)$cycloalkyl, $(C_6-C_{10})$aryl, 5- or 6-membered heteroaryl and 5- or 6-membered heterocyclyl ring containing one or two heteroatoms independently selected from the group consisting of O, N and S; and $Y_1$, $Y_2$ and $Y_3$ are as defined above.

6. The compound according to claim 2, wherein R$_4$ at each occurrence is independently selected from the group consisting of hydrogen, halogen, oxo, cyano, nitro, —NR$_5$R$_6$, —C(O)R$_5$, —C(O)NR$_5$R$_6$, —S(O)$_t$R$_7$, $(C_1-C_6)$alkyl, halo $(C_1-C_6)$alkyl, $(C_3-C_8)$cycloalkyl, hydroxy, —O$(C_1-C_6)$alkyl and —O$(C_1-C_6)$aryl.

7. A compound selected from the group consisting of:
4-(2-(2-(5-Cyclopropylthiophen-2-yl)-5-fluorophenyl) benzofuran-5-yl)butanoic acid;

4-(2-(5-Fluoro-2-(5-(1-methylcyclopropyl)thiophen-2-yl)phenyl)benzofuran-5-yl)butanoic acid;

4-(2-(2-(5-Cyclopropylthiazol-2-yl)-5-fluorophenyl)benzofuran-5-yl)butanoic acid;

4-(2-(2-(5,6-Dihydro-4H-cyclopenta[d]thiazol-2-yl)-5-fluorophenyl)benzofuran-5-yl)butanoic acid;

4-(2-(5-Fluoro-2-(4,5,6,7-tetrahydrobenzo[d]thiazol-2-yl)phenyl)benzofuran-5-yl)butanoic acid;

4-(2-(5-Fluoro-2-(isoindolin-5-yl)phenyl)benzofuran-5-yl)butanoic acid;

4-(2-(2-(5,7-Dihydrofuro[3,4-b]pyridin-3-yl)-5-fluorophenyl)benzofuran-5-yl)butanoic acid; and 4-(2-(2-(6,7-Dihydro-5H-cyclopenta[b]pyridin-3-yl)-5-fluorophenyl)benzofuran-5-yl)butanoic acid or an isotopic form, a stereoisomer, a tautomer, a pharmaceutically acceptable salt, a pharmaceutically acceptable solvate, a prodrug, a polymorph, N-oxide, S-oxide, or a carboxylic acid isostere thereof, wherein the carboxylic acid isostere is selected from:

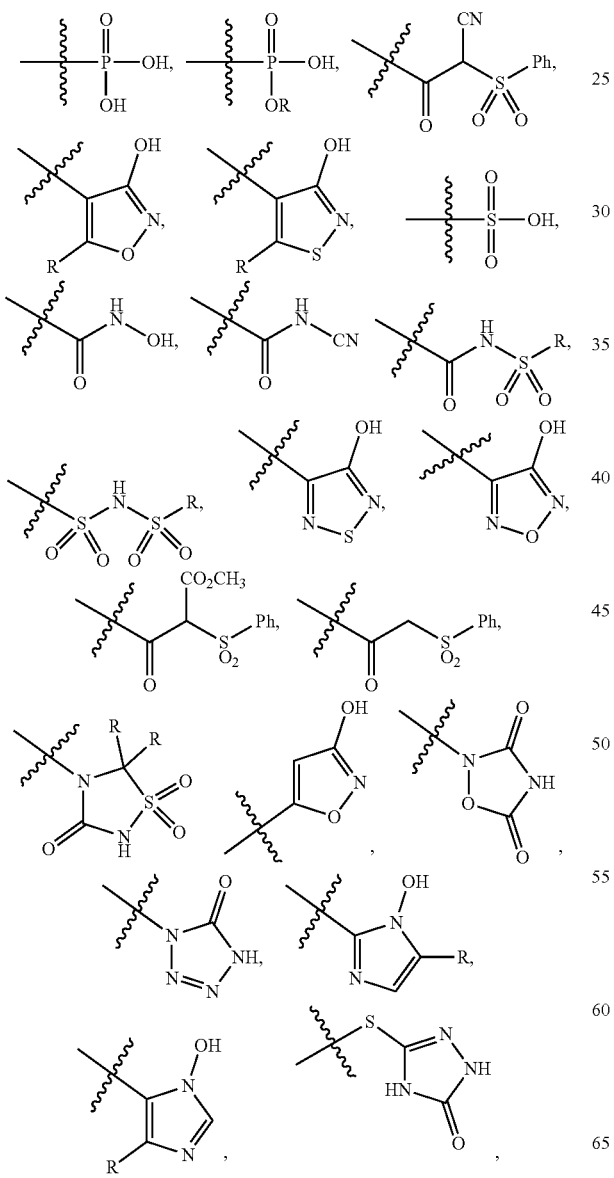

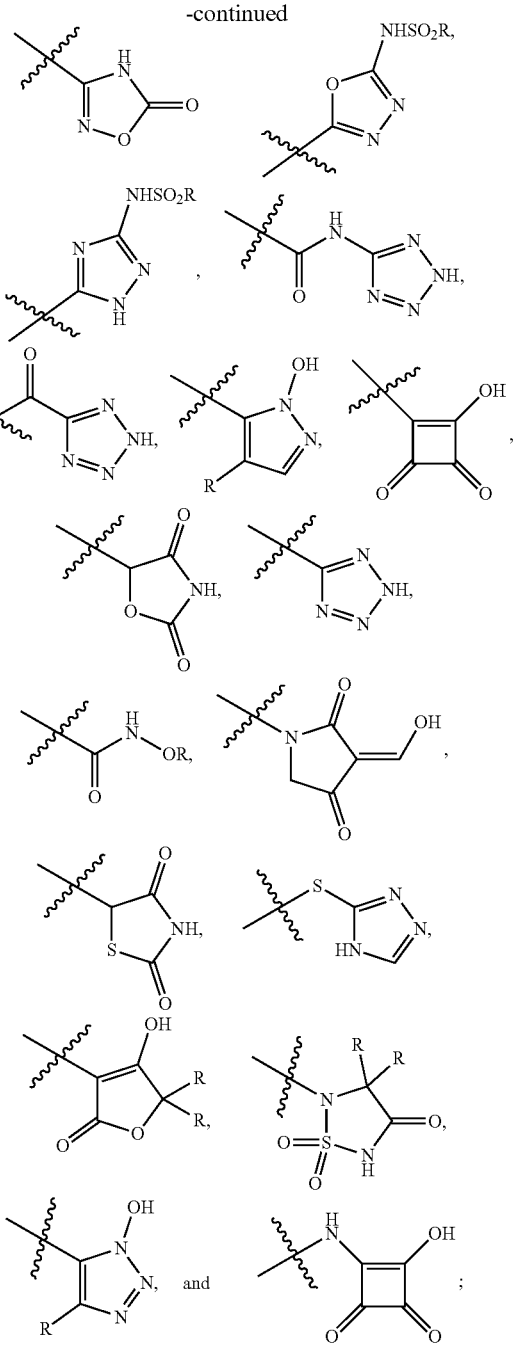

wherein R is hydrogen or $(C_1-C_3)$alkyl.

8. A pharmaceutical composition comprising a therapeutically effective amount of a compound of Formula (I) according to claim 1, or a stereoisomer, a tautomer, a pharmaceutically acceptable salt or a pharmaceutically acceptable solvate thereof; and at least one pharmaceutically acceptable carrier or excipient.

9. A method for the treatment of a disease or a disorder mediated by GPR120 comprising administering to a subject having said disease or disorder; a therapeutically effective amount of compound of Formula (I) according to claim 1, or a stereoisomer, a tautomer, a pharmaceutically acceptable salt or a pharmaceutically acceptable solvate thereof.

10. The method according to claim 9, wherein the disease or disorder mediated by GPR120 is a metabolic disorder.

11. The method according to claim 9, wherein the disease or disorder mediated by GPR120 is an inflammatory disorder.

12. A pharmaceutical composition comprising a therapeutically effective amount of a compound of claim 7, or a stereoisomer, a tautomer, a pharmaceutically acceptable salt or a pharmaceutically acceptable solvate thereof; and at least one pharmaceutically acceptable carrier or excipient.

\* \* \* \* \*